US012797479B2

(12) United States Patent
Lindsey et al.

(10) Patent No.: US 12,797,479 B2
(45) Date of Patent: *Nov. 17, 2026

(54) PROTEIN-LOADED PLGA NANOSPHERES

(71) Applicant: West Virginia University Board of Governors on behalf of West Virginia University, Morgantown, WV (US)

(72) Inventors: Brock A. Lindsey, Morgantown, WV (US); Justin E. Markel, Pittsburgh, PA (US); Ryan A. Lacinski, Bridgeville, PA (US); Jabeen Noore, Kingsville, TX (US)

(73) Assignee: West Virginia University Board of Governors on behalf of West Virginia University, Morgantown, WV (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/952,404

(22) Filed: Nov. 19, 2024

(65) Prior Publication Data

US 2025/0073343 A1 Mar. 6, 2025

Related U.S. Application Data

(63) Continuation of application No. 17/830,615, filed on Jun. 2, 2022, now Pat. No. 12,214,046, which is a
(Continued)

(51) Int. Cl.

*A61K 47/62* (2017.01)
*A61K 9/51* (2006.01)
(Continued)

(52) U.S. Cl.

CPC ............ *A61K 47/62* (2017.08); *A61K 9/5153* (2013.01); *A61K 31/43* (2013.01); *A61K 31/7036* (2013.01); *A61K 38/208* (2013.01)

(58) Field of Classification Search

None
See application file for complete search history.

(56) References Cited

U.S. PATENT DOCUMENTS 6,406,719 B1 6/2002 Farrar et al.
6,974,862 B2 12/2005 Ringeisen et al.
(Continued)

FOREIGN PATENT DOCUMENTS

CN 104622795 A 5/2015
JP 2014527980 A 10/2014
(Continued)

OTHER PUBLICATIONS

Takehisa Ishii, Kazuo Sugamura, Masataka Nakamura, and Yorio Hinuma. "Interleukin 2 (IL-2) Rapidly Induces Phosphorylation of a Cellular Protein, pp67, in an IL-2 Dependent Murine Cell Line." Biochemical and Biophysical Research Communications, vol. 135, No. 2, pp. 487-494. (Year: 1986).*
(Continued)

*Primary Examiner* — Isaac Shomer
(74) *Attorney, Agent, or Firm* — WILSON SONSINI GOODRICH & ROSATI

(57) ABSTRACT

The present disclosure provides compositions comprising protein encapsulated nanoparticles, and methods of making said compositions. In an aspect, a composition may comprise a drug delivery vector and a therapeutic substance, wherein the composition elutes at least 1.0 pg of the therapeutic substance per 100,000 particles of the drug delivery vector over a period of time under conditions of a drug delivery vector release buffer, wherein the therapeutic substance, drug delivery vector and drug delivery vector release buffer comprise a solution, wherein the solution is centrifuged and a portion stored at about 1 to 10° C., and wherein the elution of the therapeutic substance is determined by ELISA assay. This disclosure further describes a method of
(Continued)

controlling an immunophenotype in a patient suffering from a disease which impacts the immune system.

21 Claims, 21 Drawing Sheets

Related U.S. Application Data continuation of application No. PCT/US2020/063314, filed on Dec. 4, 2020.

(60) Provisional application No. 62/944,191, filed on Dec. 5, 2019.

(51) Int. Cl.

| | |
|---|---|
| ***A61K 31/43*** | (2006.01) |
| ***A61K 31/7036*** | (2006.01) |
| ***A61K 38/20*** | (2006.01) |

(56) References Cited

U.S. PATENT DOCUMENTS

| | | | |
|---|---|---|---|
| 7,041,241 | B2 | 5/2006 | Faisant et al. |
| 8,206,747 | B2 | 6/2012 | Zale et al. |
| 8,404,799 | B2 | 3/2013 | Podobinski et al. |
| 8,431,161 | B2 | 4/2013 | Kakizawa et al. |
| 8,916,206 | B2 | 12/2014 | Ishihara et al. |
| 9,308,172 | B2 | 4/2016 | Lee et al. |
| 9,393,310 | B2 | 7/2016 | Zale et al. |
| 9,724,304 | B2 | 8/2017 | Wong et al. |
| 9,972,047 | B1 | 5/2018 | Elliott et al. |
| 10,195,144 | B2 | 2/2019 | Fahmy et al. |
| 10,265,407 | B2 | 4/2019 | Mellman et al. |
| 10,420,857 | B2 | 9/2019 | Ringeisen et al. |
| 10,555,911 | B2 | 2/2020 | Zhou et al. |
| 10,751,291 | B2 | 8/2020 | Fahmy et al. |
| 10,869,935 | B2 | 12/2020 | Fotin-Mleczek et al. |
| 12,214,046 | B2 | 2/2025 | Lindsey et al. |
| 2004/0003402 | A1 | 1/2004 | McKenna, Jr. |
| 2007/0026005 | A1* | 2/2007 | Sung .................... A61K 9/1635 424/457 |
| 2009/0281888 | A1 | 11/2009 | Zai et al. |
| 2010/0172862 | A1* | 7/2010 | Correia ..................... A61P 3/10 424/130.1 |
| 2011/0125561 | A1 | 5/2011 | Marcus |
| 2012/0265001 | A1 | 10/2012 | Asmatulu et al. |
| 2015/0037427 | A1 | 2/2015 | Benita et al. |
| 2016/0303052 | A1 | 10/2016 | Fahmy |
| 2017/0151266 | A1 | 6/2017 | Kompella et al. |
| 2018/0200196 | A1* | 7/2018 | Fahmy ............... A61K 31/4178 |
| 2019/0054189 | A1 | 2/2019 | Fotin-Mleczek et al. |
| 2019/0117793 | A1 | 4/2019 | Mellman et al. |
| 2019/0151469 | A1 | 5/2019 | Fotin-Mleczek et al. |
| 2019/0343986 | A1 | 11/2019 | Ringeisen et al. |
| 2020/0179283 | A1 | 6/2020 | Fahmy et al. |
| 2023/0070180 | A1 | 3/2023 | Lindsey et al. |
| 2025/0064949 | A1 | 2/2025 | Lindsey et al. |
| 2025/0073343 | A1* | 3/2025 | Lindsey ............... A61K 9/5153 |

FOREIGN PATENT DOCUMENTS

| | | | |
|---|---|---|---|
| WO | WO-1993007861 | A1 | 4/1993 |
| WO | WO-2006093390 | A1 | 9/2006 |
| WO | WO-2013042125 | A2 | 3/2013 |
| WO | WO-2019162951 | A1 | 8/2019 |
| WO | WO-2020257297 | A1 | 12/2020 |
| WO | WO-2021113638 | A1 | 6/2021 |

OTHER PUBLICATIONS

Lina Zeng et al. "Poly(lactic-co-glycolic acid) nanoparticle-mediated interleukin-12 delivery for the treatment of diabetic retinopathy." International Journal of Nanomedicine, vol. 14, 2019, pp. 6357-6369. (Year: 2019).*

ICI Americas Inc., "The HLB System a time-saving guide to emulsifier selection." ICI Americas Inc., Wilmington, Delaware, Revised Mar. 1980, pp. 1-22. (Year: 1980).*

Darnell Sleep. "Albumin and its application in drug delivery." Expert Opinion in Drug Delivery, vol. 12(5), 2014, pp. 793-812. (Year: 2014).*

Monireh Azizi et al. "Fabrication of protein-loaded PLGA nanoparticles: effect of selected formulation variables on particle size and release profile." Journal of Polymer Research, vol. 20:110, 2013, pp. 1-14. (Year: 2013).*

ProtPi Protein Tool. https://www.protpi.ch/Calculator/ProteinTool#Results accessed Nov. 3, 2025, pp. 1-4. (Year: 2025).*

Muhammad Iqbal, Nadiah Zafar, Hatem Fessi, Abdelhamid Elaissari. "Double emulsion solvent evaporation techniques used for drug encapsulation." International Journal of Pharmaceutics, vol. 496, 2015, pp. 173-190. (Year: 2015).*

Yogesh K. Katare and Amulya K. Panda. "Influences of excipients on in vitro release and in vivo performance of tetanus toxoid loaded polymer particles." European Journal of Pharmaceutical Sciences, vol. 28, 2006, pp. 179-188. (Year: 2006).*

Allahyari, Mojgan et al. Peptide/protein vaccine delivery system based on PLGA particles. Human vaccines & immunotherapeutics 12(3):806-828 (2016).

Anticipating Needs. The Hlb System A Time Saving Guide to Emulsifier Selection. ICI Americas Inc. (pp. 1-22) (1980).

Azizi, Monireh et al. Fabrication of protein-loaded PLGA nanoparticles: effect of selected formulation variables on particle size and release profile. Journal of Polymer Research 20:110, 1-14 (2013).

Basarkar, Ashwin et al. Poly (lactide-co-glycolide)-polymethacrylate nanoparticles for intramuscular delivery of plasmid encoding interleukin-10 to prevent autoimmune diabetes in mice. Pharmaceutical research 26(1):72-81 (2009).

Budhian, Avinash et al. Haloperidol-loaded PLGA nanoparticles: systematic study of particle size and drug content. International journal of pharmaceutics 336(2):367-375 (2007).

Cappellano, Giuseppe et al. Subcutaneous inverse vaccination with PLGA particles loaded with a MOG peptide and IL-10 decreases the severity of experimental autoimmune encephalomyelitis. Vaccine 32(43):5681-5689 (2014).

Chen, Zan. 100x Penicillin Steptomycin Antibiotics Solutions for Cell Culture. Harvard Medical School, Cell Biology, Mar. 28, 2019. Avaialble at URL:https://www.biocompare.com/Product-Reviews/358399-100x-Penicillin-Streptomycin-antibiotics-solution-for-cell-culture/ pp. 1-4.

Co-pending U.S. Appl. No. 18/946,447, inventors Lindsey; Brock A et al., filed Nov. 13, 2024.

Diez, Sonsoles et al. Targeted cationic poly (D, L-lactic-co-glycolic acid) nanoparticles for gene delivery to cultured cells. Cellular and Molecular Biology Letters 14(2):347-362 (2009).

Feczko, T et al. Optimization of protein encapsulation in PLGA nanoparticles. Chemical Engineering and Processing: Process Intensification 50(8):757-765 (2011).

Gupta, Prem N. et al. M-cell targeted biodegradable PLGA nanoparticles for oral immunization against hepatitis B. Journal of drug targeting 15(10):701-713 (2007).

Ha, Sang-Jun et al. Enhanced immunogenicity and protective efficacy with the use of interleukin-12-encapsulated microspheres plus AS01B in tuberculosis subunit vaccination. Infection and immunity 74(8):4954-4959 (2006).

Hamdy, S. et al. Co-delivery of cancer-associated antigen and Toll-like receptor 4 ligand in PLGA nanoparticles induces potent CD8+ T cell-mediated anti-tumor immunity. Vaccine 26(39):5046-5057 (2008).

Hendy, R. J. et al. Long-term toxicity study of sorbitan monostearate (Span 60) in mice. Food and cosmetics toxicology 16(6):527-534 (1978).

Horwitz, David A. et al. Suppression of Murine Lupus by CD 4+ and CD 8+ Treg Cells Induced by T Cell-Targeted Nanoparticles Loaded With Interleukin-2 and Transforming Growth Factor β. Arthritis and Rheumatology 71(4):632-640 (2019).

(56) References Cited

OTHER PUBLICATIONS

Lomis, Nikita et al. Human serum albumin nanoparticles for use in cancer drug delivery: process optimization and in vitro characterization. Nanomaterials 6(6):116, 1-24 (2016).
Lu, Dongmei et al. Mixed composition films of spans and tween 80 at the Air-water interface. Langmuir 16(21):8107-8112 (2000).
McHugh, Michael D. et al. Paracrine co-delivery of TGF-β and IL-2 using CD4-targeted nanoparticles for induction and maintenance of regulatory T cells. Biomaterials 59:172-181 (2015).
Nielsen, Christina K. et al. Effects of Tween 80 on growth and biofilm formation in laboratory media. Frontiers in microbiology 7:1878, 1-10 (2016).
Park, Jason et al. Modulation of CD4+ T lymphocyte lineage outcomes with targeted, nanoparticle-mediated cytokine delivery. Molecular pharmaceutics 8(1):143-152 (2011).
Park, Min-Ho et al. Effect of chitosan on physicochemical properties of exenatide-loaded PLGA nanoparticles. Journal of Pharmaceutical Investigation 43(6):489-497 (2013).
Patel, Divya et al. A systematic review of gastric acid-reducing agent-mediated drug-drug interactions with orally administered medications. Clinical pharmacokinetics 59:447-462 (2020).
PCT/US2020/063314 International Search Report and Written Opinion dated Apr. 6, 2021.
Ryu, Ann H. et al. Use antibiotics in cell culture with caution: genome-wide identification of antibiotic-induced changes in gene expression and regulation. Scientific reports 7(1):7533, 1-28 (2017).
Sleep, Darrell. Albumin and its application in drug delivery. Expert opinion on drug delivery 12(5):793-812 (2015). Published Online Dec. 18, 2014.
U.S. Appl. No. 17/830,615 Office Action dated Jul. 24, 2024.
Varshochian, Reyhaneh et al. The protective effect of albumin on bevacizumab activity and stability in PLGA nanoparticles intended for retinal and choroidal neovascularization treatments. European Journal of Pharmaceutical Sciences 50(3-4):341-352.
Zeng, Lina et al. Poly (lactic-co-glycolic acid) nanoparticle-mediated interleukin-12 delivery for the treatment of diabetic retinopathy. International journal of nanomedicine:6357-6369 (2019).
Ashjari, Mohsen. et al. Controlling the morphology and surface property of magnetic/cisplatin-loaded nanocapsules via W/O/W double emulsion method. Colloids and Surfaces A: Physicochemical and Engineering Aspects 408:87-96 (2012).
Bilati, Ugo. et al. Poly (D, L-lactide-co-glycolide) protein-loaded nanoparticles prepared by the double emulsion method—processing and formulation issues for enhanced entrapment efficiency. Journal of Microencapsulation 22(2):205-214 (2005).
Cohen-Sela, Einat. et al. A new double emulsion solvent diffusion technique for encapsulating hydrophilic molecules in PLGA nanoparticles. Journal of Controlled Release 133(2):90-95 (2009). Published Online Sep. 24, 2008.
Craythorne, N.L. et al. Stabilisation of W/O/W nanoemulsions through the use of stabilising agents poly(vinyl alcohol) and nonionic surfactants tween 20 and Span 80. Journal of Pharmacy and Pharmaceutical Sciences 14(3):216s-217s (2011).
U.S. Appl. No. 18/946,447 Office Action dated Mar. 3, 2025.
Varshochian, Reyhaneh. et al. Albuminated PLGA nanoparticles containing bevacizumab intended for ocular neovascularization treatment. Journal of biomedical materials research. Part A 103(10):3148-3156 (2015).
Zambaux, M. F. et al. Influence of experimental parameters on the characteristics of poly (lactic acid) nanoparticles prepared by a double emulsion method. Journal of Controlled Release 50(1-3):31-40 (1998).
Goel, Anjali et al. Effect of PVP, PVA and POLE surfactants on the size of iridium nanoparticles. Open Journal Of Inorganic Chemistry 2(3):19763, 1-7 (2012).
U.S. Appl. No. 18/946,447 Office Action dated Jun. 11, 2025.
U.S. Appl. No. 18/946,447 Office Action dated Jun. 2, 2026.

* cited by examiner

| T cell Subset | Dose | Baseline (% Tim3+PD1+) | 48h (% Tim3+PD1+) |
|---|---|---|---|
| Helper T cell | L | 1.36 ± 0.23 | 2.39 ± 0.38 |
| | H | 1.80 ± 0.79 | 3.87 ± 1.50 |
| Cytotoxic T cell | L | 6.84 ± 0.39 | 9.15 ± 0.61 |
| | H | 6.70 ± 2.50 | 15.87 ± 5.12 |
| Regulatory T cell | L | 4.05 ± 0.59 | 6.25 ± 1.13 |
| | H | 5.18 ± 1.74 | 8.33 ± 2.43 |

| Dose | Baseline (% PMN-MDSCs) | 48h (% PMN-MDSCs) |
|---|---|---|
| L | 23.85 ± 4.95 | 67.10 ± 11.74 |
| H | 16.39 ± 2.00 | 78.93 ± 6.49 |

| Dose | Baseline (% NK cells) | 48h (% NK cells) |
|---|---|---|
| L | 13.40 ± 0.71 | 11.65 ±2.78 |
| H | 13.50 ± 1.41 | 7.00 ± 1.60 |

PROTEIN-LOADED PLGA NANOSPHERES

CROSS-REFERENCE TO RELATED APPLICATIONS

This application is a Continuation of U.S. application Ser. No. 17/830,615 filed Jun. 2, 2022, which is a continuation of International Application No. PCT/US2020/063314, filed Dec. 4, 2020, which claims the benefit of U.S. Provisional Application No. 62/944,191, filed Dec. 5, 2019, each of which is incorporated herein by reference in its entirety.

STATEMENT REGARDING FEDERALLY SPONSORED RESEARCH

This application was made with government support under grant numbers 2U54GM104942-02, S10OD016165, P30GM103488, and P20GM103434 awarded by the National Institute of Health/National Institute of General Medical Sciences. The government has certain rights in this invention.

FIELD

Various embodiments disclosed herein relate generally to preparation of protein-containing nanospheres.

Various embodiments disclosed herein relate to immunophenotyping for immune analysis.

BACKGROUND

Immunostimulation is an important mechanism that 1) can prevent malignant cells from proliferating and/or forming metastases and 2) can clear viral and bacterial infections. Immunotherapy cancer treatment can involve monoclonal antibody blockade of specific immune regulatory checkpoints, including the Programmed Death-Ligand 1 (PD-L1) and Cytotoxic T-Lymphocyte-Associated Protein 4 (CTLA-4) axes.

Historically, the focus has been on the tumor microenvironment and the immune response. However, a systemic response can provide a lasting immunological response and cure disease. Many groups have looked at the immunophenotyping of treatments to help to explain what is happening immunologically to the patient in real time. This information will play an important role as immunotherapeutics for multiple diseases become more mainstream and developing a living database of these responses will push the process forward tremendously.

Preclinical studies have shown that interleukins can induce antitumor responses against many malignancies. Interleukin-12 (IL-12), an immunostimulatory cytokine with antitumor activity that is maximized when given systemically, can induce such antitumor responses. While high-dose IL-12 administration can have toxic side effects, low doses of IL-12 can be considered safe.

Poly(D,L-lactic acid-co-glycolic acid) (PLGA) drug delivery vectors are FDA approved and can elute a wide variety of substances as the polymer breaks down. For therapeutic purposes, encapsulating peptides, potentially including immunostimulatory interleukin proteins, within PLGA nanospheres can allow for systemic delivery and tissue deposition without the need for toxic loading doses. In order to be used in systemic settings, nanospheres can achieve safe and effective blood-borne travel through the macro- and micro-vasculature of an organism.

SUMMARY

In light of the present need for improved methods of cytokine administration, a brief summary of various exemplary embodiments are presented. Some simplifications and omissions can be made in the following summary, which is intended to highlight and introduce aspects of certain embodiments disclosed herein, but not to limit the scope of the disclosure. Detailed descriptions of various embodiments adequate to allow those of ordinary skill in the art to make and use the concepts disclosed herein will follow in later sections.

According to various embodiments disclosed herein, a protein can be encapsulated in a nanosphere. This encapsulation process can be performed by making a double emulsion, where a first water phase can be emulsified in an oil phase, and the oil phase is emulsified in a second water phase. The protein can be a cytokine, which can be a small protein (~5-20 kDa) that plays a role in cell signaling. Suitable cytokines include:

- interleukins, produced by T-helper cells;
- lymphokines, produced by lymphocytes;
- monokines, produced exclusively by monocytes;
- interferons, involved in antiviral responses;
- colony stimulating factors, which support the growth of cells in semisolid media; and
- chemokines, which mediate chemoattraction between cells.

In various embodiments, the protein encapsulated in the nanosphere can be cytokines with three-dimensional structures having a bundle of four ac-helices, which can be interferons, interleukins, e.g., interleukin-2 or interleukin-12, or non-immunological cytokines, including erythropoietin and thrombopoietin. The protein encapsulated in the nanosphere can be interleukin-12 (IL-12).

The oil phase can be prepared by dissolving from 2.5% w/v to 17% w/v of poly(lactic acid-co-glycolic acid) (PLGA) in an organic solvent. A first aqueous phase can be made by suspending a protein in an aqueous medium. Finally, a second aqueous phase can be made by dissolving polyvinyl alcohol (PVA) in water.

The PLGA can comprise from 50% to 90% lactide, and the organic solvent can be a halogenated C1-C3 organic solvent, a C2-C3 nitrile solvent, a C2-C5 alkyl ester solvent, a C3 to C5 ketone solvent, or a mixture thereof. The PLGA can comprise from 75% to 90% lactide. The PLGA can comprise from 50% to 75% lactide, and the organic solvent can be a halogenated C1-C3 organic solvent, acetonitrile, a C3 to C4 ketone solvent, or a mixture thereof. In various embodiments, the PLGA comprises from 50% to 90% lactide, and the organic solvent can be acetonitrile, acetone, ethyl acetate, or dichloromethane.

The protein-containing aqueous medium can be added to the oil phase to form a first emulsion, with agitation. The first emulsion can be added to the PVA-containing aqueous phase to form a second emulsion, with agitation. The organic solvent can then be evaporated from the second emulsion to form an aqueous solution; and PLGA nanospheres containing the protein from the second aqueous phase can be recovered from the aqueous solution.

In an aspect, this disclosure describes a composition comprising poly(D,L-lactic acid-co-glycolic acid) (PLGA) nanospheres and a therapeutic substance, wherein at least a portion of the therapeutic substance can elute from the composition more than 72 hours after placement of the composition in a solution.

In various embodiments, at least a portion of the therapeutic substance can elute from the composition more than 96, 120, 144, 168, 192, 216, 240, 264, 288, 312, 336 hours after placement of the composition in a solution. At least a portion of the therapeutic substance can elute from the composition between 72 and 288 hours after placement of the composition in a solution. The therapeutic substance can be IL-12. The solution can be a mammalian serum and about 100 units/mL Penicillin-Streptomycin (Pen-Strep) in Phosphate-Buffered Salt Solution (DPBS).

In an aspect, this disclosure describes a composition comprising poly(D,L-lactic acid-co-glycolic acid) (PLGA) nanospheres and IL-12, wherein IL-12 can be incorporated into the PLGA nanospheres with an encapsulation efficiency of at least 2%.

In various embodiments, IL-12 can be incorporated into the PLGA nanospheres with an encapsulation efficiency of at least 10%, 20%, 40%, 50%, 60%, 70%, 80%, 90%, 100%. IL-12 can be incorporated into the PLGA nanospheres with an encapsulation efficiency of from about 2% to about 40%. The IL-12 can be bioactive IL-12.

In an aspect, this disclosure describes a composition comprising a drug delivery vector and a therapeutic substance, wherein the composition can elute at least 1.0 pg of the therapeutic substance per 100,000 particles of the drug delivery vector under conditions of a drug delivery vector release buffer, wherein the composition continues to elute therapeutic substance over more than 3 days, wherein the therapeutic substance, drug delivery vector and drug delivery vector release buffer comprise a solution, wherein the solution is centrifuged and a portion stored at about 1 to 10° C., and wherein the elution of the therapeutic substance is determined by ELISA assay. The composition can comprise a surfactant. The surfactant can be Tween 80 and Span 60. The composition can comprise In various embodiments, the drug delivery vector can comprise poly(D,L-lactic acid-co-glycolic acid) (PLGA). The therapeutic substance can be a protein. The protein can be a cytokine. The cytokine can be IL-12. The drug delivery vector release buffer can comprise about 10% Fetal Bovine Serum Qualified Heat Inactivated (HI-FBS) and about 100 units/mL Penicillin-Streptomycin (Pen-Strep) in Phosphate-Buffered Salt Solution (DPBS), species specific whole serum, species specific engineered serum albumin or species specific whole fetal serum.

In an aspect, this disclosure describes a composition comprising protein loaded poly(D,L-lactic acid-co-glycolic acid) (PLGA) nanospheres, wherein the nanospheres can comprise a diameter of about 100 to 1000 nm, a surfactant, and a species specific whole serum, engineered or native serum albumin.

In various embodiments, the protein can comprise IL-12. The surfactant can comprise Tween 80 and Span 60.

In an aspect, this disclosure describes a method of making a protein encapsulated nanosphere, comprising determining the rate of dissociation of the protein with increasing time and/or increasing sonication wattage, comparing the rate of dissociation of the protein with a rate of formation of the nanosphere with increasing time and/or sonication wattage, determining a time and sonication wattage at a point of intersection between the rate of dissociation of the protein and the rate of formation of the nanosphere, preparing a first phase by dissolving of PLGA in a solvent with a first surfactant, preparing a second phase by dissolving an alcohol in water with a second surfactant and a mammalian serum, suspending the component in an aqueous medium, forming a first emulsion comprising the aqueous medium and the first phase, forming a second emulsion comprising the first emulsion and the second phase and sonicating the second emulsion for the time and sonication power determined at the point of intersection, evaporating the solvent from the second emulsion to form an aqueous solution, and recovering PLGA nanospheres containing the component from the aqueous solution.

In an aspect, this disclosure describes a method of encapsulating a component in a nanosphere, comprising preparing a first phase by dissolving of poly(lactic acid-co-glycolic acid) (PLGA) in a solvent, preparing a second phase by dissolving an alcohol in water, suspending the component in an aqueous medium, forming a first emulsion comprising the aqueous medium and the first phase, forming a second emulsion comprising the first emulsion and the second phase, evaporating the solvent from the second emulsion to form an aqueous solution, and recovering PLGA nanospheres containing the component from the aqueous solution.

In various embodiments, the component can comprise a protein. The protein can comprise IL-12. The component can comprise a surfactant and a mammalian serum. The PLGA can comprise from 50% to 90% lactide, and the solvent can be selected from the group consisting of halogenated C1-C3 organic solvents, C2-C3 nitrile solvents, C2-C5 alkyl ester solvents, C3 to C5 ketone solvents, and mixtures thereof. The solvent can be acetonitrile, acetone, ethyl acetate, or dichloromethane. The PLGA can comprise from 75% to 90% lactide. The PLGA can comprise from 50% to 75% lactide, and the solvent can be selected from the group consisting of halogenated C1-C3 organic solvents, acetonitrile, C3 to C4 ketone solvents, and mixtures thereof. The method can comprise adding the aqueous medium to the first phase to form the first emulsion, and agitating the first emulsion with a tissue homogenizer at a rate of 13,000 RPM to 20,000 RPM and adding the first emulsion to the second phase to form the second emulsion, and agitating the second emulsion with a tissue homogenizer at a rate of 13,000 RPM to 20,000 RPM. The method can comprise adding the aqueous medium to the first phase to form the first emulsion, and agitating the first emulsion by sonication and adding the first emulsion to the second phase to form the second emulsion, and agitating the second emulsion by sonication. The method can comprise agitating the first emulsion comprises sonication at a power level of 30 W to 50 W, for a period of time of 5 sec to 30 sec, and agitating the second emulsion comprises sonication at a power level of 30 W to 50 W, for a period of time of 5 sec to 30 sec. The protein can be a cytokine or a globular protein. The protein can be a cytokine selected from the group consisting of interleukins, lymphokines, monokines, interferons, colony stimulating factors, and chemokines. The cytokine can be selected from the group consisting of interleukins and non-immunological cytokines. The protein can be a cytokine having an N-terminal signal sequence, a four-helix bundle comprising four helices labeled A through D, and no C-terminal extension following the D helix. The cytokine can be a granulocyte-macrophage colony-stimulating factor, a granulocyte colony-stimulating factor, interferon alpha-1, interferon beta, interferon gamma, interferon kappa, interferon tau-1, interferon omega-1, or an interleukin selected from the group consisting of IL-2, IL-3, IL-4, IL-5, IL-5, IL-6, IL-7, IL-9, IL-10, IL-11, IL-12, the alpha chain of IL-12, IL-13, IL-15, IL-19, IL-20, IL-21, IL-22, IL-23, IL-24, IL-26, and IL-27. The protein can be an immunological cytokine that either: a) enhances cellular immune responses, or b) enhances antibody responses. The cytokine can be an immunological cytokine that enhances cellular immune responses, selected from the group consisting of TNFα, IFN-γ, and interleukin-12. The cytokine can be IL-12. The cytokine can be an immunological cytokine that enhances antibody responses, selected from the group consisting of TGF-β, IL-4, IL-10, and IL-13. The first and second emulsions can each be agitated with a tissue homogenizer at a rate of 13,000 RPM to 20,000 RPM, and IL-12 is incorporated into the PLGA nanospheres with an encapsulation efficiency of about 0.5% to about 2.1%. The first and second emulsions can each be agitated with sonication at a power level of 30 W to 50 W, for a period of time of 5 sec to 30 sec, and IL-12 is incorporated into the PLGA nanospheres with an encapsulation efficiency of about 4.5% to about 10%. The second phase can contain polyvinyl alcohol and mammalian serum. The first phase can contain the first surfactant, and/or the second phase can contain the second surfactant. The first surfactant can be a sorbitan fatty acid ester, and/or the second surfactant can be a polyoxyethylene sorbitan fatty acid ester. The second phase can contain polyvinyl alcohol and fetal serum.

In various embodiments, a first portion of the protein can be adsorbed onto a surface of the nanosphere, a second portion of the protein can be incorporated into the PLGA matrix at a core of the nanosphere, and the nanosphere can comprise at least one additive selected from the group consisting of mammalian serum albumin, trehalose, the first surfactant, and the second. The nanosphere can comprise mammalian serum albumin and a surfactant.

In various embodiments, this disclosure describes a dosage form comprising a plurality of nanospheres produced by the methods described, each nanosphere comprising a PLGA matrix and a protein, wherein a first portion of the protein can be adsorbed onto a surface of the nanosphere, and a second portion of the protein is incorporated into the PLGA matrix at a core of the nanosphere. The protein can be IL-12 and the IL-12 can be incorporated into the nanosphere with an encapsulation efficiency of at least 2%.

In an aspect, this disclosure describes method of encapsulating a protein in a nanosphere, comprising preparing an oil phase by dissolving from 2.5% w/v to 17% w/v of poly(lactic acid-co-glycolic acid) (PLGA) in an organic solvent, optionally containing a first surfactant, preparing an aqueous phase containing polyvinyl alcohol and at least one additive selected from the group consisting of mammalian serum, trehalose, and a second surfactant; suspending the protein in an aqueous medium, adding the aqueous medium to the oil phase to form a first emulsion, and agitating the first emulsion, adding the first emulsion to the aqueous phase to form a second emulsion, and agitating the second emulsion, evaporating the organic solvent from the second emulsion to form an aqueous solution, and recovering poly(lactic acid-co-glycolic acid) nanospheres containing the protein from the aqueous solution.

In an aspect, this disclosure describes method of controlling an immunophenotype in a patient suffering from a disease which impacts the immune system, comprising (a) determining a disease state of a patient, where the disease state includes a diagnosis and an initial immunophenotype, (b) comparing the disease state of the patient to a plurality of disease states within a database, where each disease state in the database includes a diagnosis, an initial immunophenotype, and a treatment protocol, and (c) based on the comparing step (b), selecting a treatment protocol from the database, where the treatment protocol involves administering an immunomodulating drug.

In various embodiments, the method can comprise (d) administering the immunomodulating drug to the patient, (e) after step (d), monitoring the patient's immunophenotype as a function of time, and adjusting administration of the immunomodulating drug if the patient's immunophenotype falls outside a desired range.

In various embodiments, the protein-containing aqueous medium can be added to the oil phase to form a first emulsion, with agitation by a tissue homogenizer at a rate of 13,000 RPM to 20,000 RPM. The first emulsion can be added to the PVA-containing aqueous phase to form a second emulsion, with agitation by a tissue homogenizer at a rate of 13,000 RPM to 20,000 RPM. The organic solvent can then be evaporated from the second emulsion to form an aqueous solution; and PLGA nanospheres containing the protein from the second aqueous phase can be recovered from the aqueous solution.

In various embodiments, the protein in the protein-containing aqueous medium can be a cytokine. Suitable cytokines include interleukins, lymphokines, monokines, interferons, colony stimulating factors, and chemokines. The protein can be a cytokines with a three-dimensional structures having a bundle of four ac-helices, e.g., interleukins, e.g., interleukin-2 or interleukin-12, or non-immunological cytokines, including erythropoietin and thrombopoietin.

In various embodiments, the protein in the protein-containing aqueous medium can be IL-12. IL-12 can be incorporated into PLGA nanospheres by agitating the first and second emulsions with a tissue homogenizer at a rate of 13,000 RPM to 20,000 RPM. IL-12 can be incorporated into the resulting PLGA nanospheres with an encapsulation efficiency of about 0.5% to about 2.1%.

In various embodiments, the protein-containing aqueous medium can be added to the oil phase to form a first emulsion, with agitation by ultrasonication. The first emulsion can be added to the PVA-containing aqueous phase to form a second emulsion, with agitation by sonication. Agitation during formation of either or both of the first and second emulsions can comprise sonication at a power level of 30 W to 50 W, 30 W to 40 W, or 40 W to 50 W, for a period of time of 5 sec to 30 sec, 10 sec to 30 sec, 10 sec to 20 sec, or 10 sec to 15 sec. The organic solvent can then be evaporated from the second emulsion to form an aqueous solution; and PLGA nanospheres containing the protein from the second aqueous phase can then be recovered from the aqueous solution.

In various embodiments, the protein-containing aqueous medium can be added to the oil phase to form a first emulsion, with agitation by a tissue homogenizer at a rate of 13,000 RPM to 20,000 RPM. The first emulsion can be added to the PVA-containing aqueous phase to form a second emulsion, with agitation by sonication at a power level of 30 W to 50 W, 30 W to 40 W, or 40 W to 50 W, for a period of time of 5 sec to 30 sec. The organic solvent can then be evaporated from the second emulsion to form an aqueous solution; and PLGA nanospheres containing the protein from the second aqueous phase can be recovered from the aqueous solution.

In various embodiments, the protein in the protein-containing aqueous medium can be IL-12. IL-12 can be incorporated into PLGA nanospheres by sonication at a power level of 30 W to 50 W, for a period of time of 10 sec to 20 sec. IL-12 can be incorporated into the resulting PLGA nanospheres with an encapsulation efficiency of about 2% to about 85%, about 4.5% to about 70%, about 5% to 60%, about 7% to about 50%, about 8% to about 40%, about 10% to 30%, or about 5% to 10%.

Various embodiments disclosed herein are directed to a nanosphere comprising a poly(lactic acid-co-glycolic acid) matrix and a protein, where a first portion of the protein can be adsorbed onto a surface of the nanosphere and a second portion of the protein can be incorporated into the poly (lactic acid-co-glycolic acid) matrix at a core of the nanosphere. The nanosphere can be produced by making a double emulsion, where a first, protein-containing, water phase can be emulsified in an oil phase, and the oil phase can be then emulsified in a second water phase. The protein can be a cytokine, such as IL-12. The IL-12 can be incorporated into the nanosphere with an encapsulation efficiency of about 0.5% to about 85%, about 1% to about 70%, about 2% to 60%, about 3% to about 50%, about 4% to about 40%, about 5% to 30%, about 0.5% to 10%, about 1% to 8%, or about 2% to 5%. IL-12 can be incorporated into the PLGA nanospheres with an encapsulation efficiency of at least 0.5%, 1%, 2%, 3%, 4%, 5%, 6%, 7%, 8%, 9% 10%, 20%, 40%, 50%, 60%, 70%, 80%, 90%, 99%, or 100%.

Various embodiments disclosed herein relate to a method of encapsulating a protein in a nanosphere, by preparing an oil phase by dissolving from 2.5% w/v to 17% w/v of poly(lactic acid-co-glycolic acid) (PLGA) in an organic solvent containing an optional first surfactant; preparing an aqueous phase containing polyvinyl alcohol and at least one additive selected from the group consisting of mammalian whole serum, recombinant/native mammalian albumin, trehalose, and a second surfactant; and suspending the protein in an aqueous medium. The first surfactant can be a sorbitan fatty acid ester. The aqueous medium can be added to the oil phase to form a first emulsion. The first emulsion can be agitated, and the first emulsion can be added to the aqueous phase to form a second emulsion, which can then be agitated. The organic solvent can be evaporated from the second emulsion to form an aqueous solution; and poly (lactic acid-co-glycolic acid) nanospheres containing the protein can be recovered from the aqueous solution. The aqueous phase can contain polyvinyl alcohol and mammalian serum, e.g., fetal serum. The aqueous phase can contain polyvinyl alcohol and the second surfactant, where the first surfactant can be a sorbitan fatty acid ester; and the second surfactant can be a polyoxyethylene sorbitan fatty acid ester.

Various embodiments disclosed herein relate to a nanosphere comprising a poly(lactic acid-co-glycolic acid) matrix and a protein, where a first portion of the protein can be adsorbed onto a surface of the nanosphere; and a second portion of the protein can be incorporated into the poly (lactic acid-co-glycolic acid) matrix at a core of the nanosphere. The nanosphere can further comprise at least one additive selected from the group consisting of mammalian serum albumin, trehalose, and a surfactant. The nanosphere can comprise mammalian serum albumin, mammalian recombinant/native albumin, and a surfactant. The nanosphere can comprise mammalian whole serum, mammalian recombinant/native albumin, a first surfactant, and a second surfactant.

In many disease states, e.g., cancer and autoimmune disorders, the human immune system can be in constant flux. In order to treat such diseases, it can be beneficial for a medical practitioner to assess the immune system of a patient in real time, and to follow the immune system status over time. When cancer, infections, and/or autoimmune disorders are being treated with immunomodulating agents, regardless of whether they are immunosuppressive or immunostimulating, it can be beneficial for the medical practitioner to be able to follow the impact of such agents on the immune system.

Various embodiments disclosed herein relate to a method allowing systemic analysis of the immune system from a blood draw or a finger stick blood draw that can be analyzed at a testing site. The response of the immune system to a disease state, e.g., cancer or an autoimmune disease, can be analyzed at a selected time, and the immune response to a treatment protocol can be followed over the course of a disease or treatment.

This diagnostic method can be useful in the treatment, surveillance, and diagnosis of many diseases, including cancer, autoimmune diseases, and infections. As immunomodulating agents become more common, the method can provide the medical practitioner with the ability to assess the status of the immune system at a specific time in the pathogenesis of a disease, and can allow prediction as to which immomodulating treatment can be most effective in combating the disease. This can increase the overall effectiveness of treatment, and can allow improved assessment of the immune status of the patient in the disease process. This information can also be organized in a living database of immune profiles across disease specific categories that can allow practitioners to be more informed on the treatments they will be giving based on previous experiences.

Various embodiments disclosed herein relate to a method of controlling an immunophenotype in a patient suffering from a disease which impacts the immune system, including steps of determining an initial immunophenotype, or immune status, of a patient; and either:

administering a first drug which stimulates the immune system if the initial immunophenotype shows immunosuppression; or administering a second drug which suppresses the immune system if the initial immunophenotype shows overstimulation of the immune system.

After administering the selected drug, the patient's immunophenotype can be monitored as a function of time; and administration of the first and/or second drug can be adjusted if the patient's immunophenotype falls outside a desired range.

Various embodiments disclosed herein relate to a method of controlling an immunophenotype in a patient suffering from a disease which impacts the immune system, by determining a disease state of a patient, where the disease state includes a diagnosis and an initial immunophenotype; and comparing the disease state of the patient to a plurality of disease states within a database, where each disease state in the database includes a diagnosis, an initial immunophenotype, and a treatment protocol. Based on the comparison between the patient's disease state and disease states and treatment protocols from the database, a treatment protocol can be selected from the database, where the treatment protocol involves administering an immunomodulating drug. The method can include administering the immunomodulating drug to the patient; monitoring the patient's immunophenotype as a function of time after administering the drug; and adjusting administration of the immunomodulating drug if the patient's immunophenotype falls outside a desired range.

Immunophenotyping of a patient's blood sample can involve the ability to analyze and assess the data appropriately. This system can allow the appropriate dosing, treatment, and corrections to be made across several disease states. As the collection of data increases the growing database can also be able help direct medical professionals to diagnosis, treat, and dose immunotherapeutics in the broadest sense.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

DETAILED DESCRIPTION

Figure 1A:
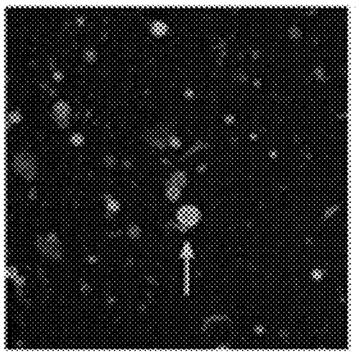
FIGS. 1A and 1B show distribution of fluorescein isothiocyanate-labeled bovine serum albumin protein in a PLGA nanosphere.

As used in the specification and claims, the singular form "a", "an", and "the" include plural references unless the context clearly dictates otherwise. For example, the term "a sample" includes a plurality of samples, including mixtures thereof.

A "nanosphere," or "nanoparticle" can be an ultrafine particle. Such a particle can be made from a variety of materials, including but not limited to Poly(D,L-lactic acid-co-glycolic acid) (PLGA).

PLGA drug delivery vectors are FDA approved and can elute a wide variety of substances as the polymer coating breaks down into Krebs cycle intermediates. Drug solubility, bioavailability, and stability can all be altered by the organic coating allowing for large shifts in the pharmacokinetic and pharmacodynamics properties of the encapsulated substrate. For tumor and infection therapeutic purposes, encapsulating IL-12 within PLGA nanospheres can allow for systemic delivery and tissue deposition without the need for toxic loading doses. The negatively charged surface can be repelled by the glycocalyx, and along with their smaller size allows for increased deposition in the interstitial space where they can elute their contents undisturbed. To date, however, the successful encapsulation of IL-12 within sub-micron scale PLGA particles has not been achieved. Nanospheres can provide safe and effective blood-borne travel through the microvasculature of an organism (capillaries can be approximately 4-9 microns in diameter) with minimal risk of forming emboli.

A PLGA nanosphere with an encapsulated protein can be created by:

- preparing an oil phase by dissolving from 2.5% w/v to 17% w/v of PLGA in an organic solvent;
- preparing an aqueous phase by dissolving from 1% w/v to 3% w/v of polyvinyl alcohol in an aqueous solvent;
- suspending a protein in an aqueous medium;
- adding the aqueous medium to the oil phase to form a first emulsion, and homogenizing the first emulsion;
- adding the first emulsion to the aqueous phase to form a second emulsion, and
- homogenizing the second emulsion;
- evaporating the organic solvent from the second emulsion to form an aqueous solution;
- and recovering PLGA nanospheres containing the protein from the aqueous solution.

Proteins

In various embodiments, the protein can be a cytokine selected from the group consisting of interleukins, lymphokines, monokines, interferons, colony stimulating factors, and chemokines. The cytokine can be an interleukin or a non-immunological cytokine.

The cytokine can have an N-terminal signal sequence, a four-helix bundle comprising four helices labeled A through D, and an optional C-terminal extension following the D helix. The cytokine can lack a substantial C-terminal extension, and may be a granulocyte-macrophage colony-stimulating factor, a granulocyte colony-stimulating factor, interferon alpha-1, interferon beta, interferon gamma, interferon kappa, interferon tau-1, interferon omega-1, or an interleukin (IL) selected from the group consisting of IL-2, IL-3, IL-4, IL-5, IL-5, IL-6, IL-7, IL-9, IL-10, IL-11, the alpha chain of IL-12, IL-12, IL-13, IL-15, IL-19, IL-20, IL-21, IL-22, IL-23, IL-24, IL-26, and IL-27.

In various embodiments, the cytokine can be an immunological cytokine that either enhances cellular immune responses; or enhances antibody responses. If the cytokine is an immunological cytokine that enhances cellular immune responses, the cytokine can be selected from the group consisting of tumor necrosis factor-alpha (TNFoc), interferon-gamma (IFN-'), and interleukin-12 (which can stimulate the production of IFN-' and TNFoc). If the cytokine is an immunological cytokine that enhances antibody responses, the cytokine can be selected from the group consisting of transforming growth factor beta (TGF-f3), IL-4, IL-10, and IL-13.

In various embodiments, the protein to be encapsulated in a nanosphere can be a globular protein. Suitable globular proteins can include serum albumin proteins; enzymes, e.g., esterases; hormones, e.g., insulin; and transporter proteins.

In various embodiments, PLGA nanospheres can be used to encapsulate pharmaceutical active ingredients; vitamins; nutraceutical active ingredients, e.g., phytochemicals; and organic dyes or contrast agents. PLGA nanospheres can be used for controlled release of a variety of drugs, including poorly soluble Class III and Class IV drugs.

Methods of Making Nanoparticles

To create the oil phase, from 2.5% w/v to 17% w/v of PLGA can be dissolved in an organic solvent. The PLGA may contain from 50% to 90% lactide, from 65% to 90% lactide, or from 75% to 90% lactide. The organic solvent can be a halogenated C1-C3 organic solvent, e.g., dichloromethane, chloroform, or 1,1,1-trichloroethane; a C2-C3 nitrile solvent, e.g., acetonitrile or propionitrile; or a C2-C5 alkyl ester solvent, e.g. ethyl acetate or butyl acetate; or a C3 to C5 ketone solvent, e.g., acetone or pentanone. The organic solvent can be a semipolar solvent with a dipole moment between 1.1 and 3.5. The oil phase can be made by dissolving PLGA in the organic solvent at room temperature (RT) with stirring, where the stirring can be at 300 to 600 RPM, 350 to 550 RPM, or 425 to 500 RPM.

In various embodiments, the solvent selection can be made based on a lactide content in the PLGA. If the PLGA contains 75% to 90% lactide, the organic solvent can be a halogenated C1-C3 organic solvent, C2-C3 nitrile solvent, or a C2-C5 alkyl ester solvent, or a C3 to C5 ketone solvent. If the PLGA contains less than 75% lactide, the organic solvent can be a halogenated C1-C3 organic solvent, acetonitrile, or a C3 to C4 ketone solvent.

To create the aqueous phase of the emulsion, from 1% w/v to 3% w/v of polyvinyl alcohol (PVA) can be dissolved in an aqueous solvent, which can be water or a buffered saline solution, e.g., phosphate buffered saline.

Next, a protein, e.g., IL-12 or bovine serum albumin, can be suspended in an aqueous medium, which can be a buffered saline solution, e.g., phosphate buffered saline, and the resulting protein suspension can be added to the PLGA-containing oil phase, which can be subjected to rapid stirring, e.g., 10,000 to 20,000 RPM; 12,000 to 19,500 RPM; 13,000 to 19,000 RPM; 15,000 to 18,000 RPM, or 16,000 to 17,500 RPM, to produce a first emulsion. Alternatively, the protein suspension can be added to the PLGA-containing oil phase with sonication to produce the first emulsion.

The first emulsion can be then added to the PVA aqueous phase with rapid stirring, e.g., 10,000 to 20,000 RPM; 12,000 to 19,500 RPM; 13,000 to 19,000 RPM; 15,000 to 18,000 RPM, or 16,000 to 17,500 RPM; with homogenization; or with sonication to produce a second emulsion. The organic solvent can be then evaporated from the second emulsion. PLGA nanoparticles containing the protein from the aqueous medium can be recovered by centrifugation, and flash-frozen in liquid nitrogen and/or lyophilized.

Without being bound by any theory, the use of sonication over time can increase formation of nanoparticles by increasing the number of nanoparticles, decreasing the size of said nanoparticles, and increasing the uniformity of the nanoparticles. Further, higher sonication wattage can also increase the formation of nanoparticles. Proteins, however, can dissociate when exposed to sonication over time, particularly at higher sonication wattage over longer periods of time. Thus, as disclosed here, the parameters of sonication wattage and time in the creation of protein loaded nanoparticles can be optimized for individual protein variations.

Figure 1B:
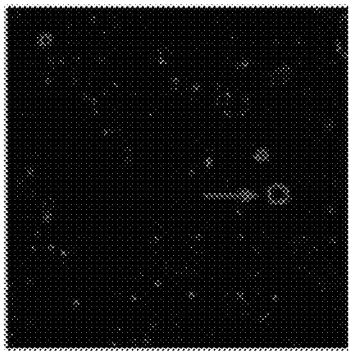
Figure 1C:
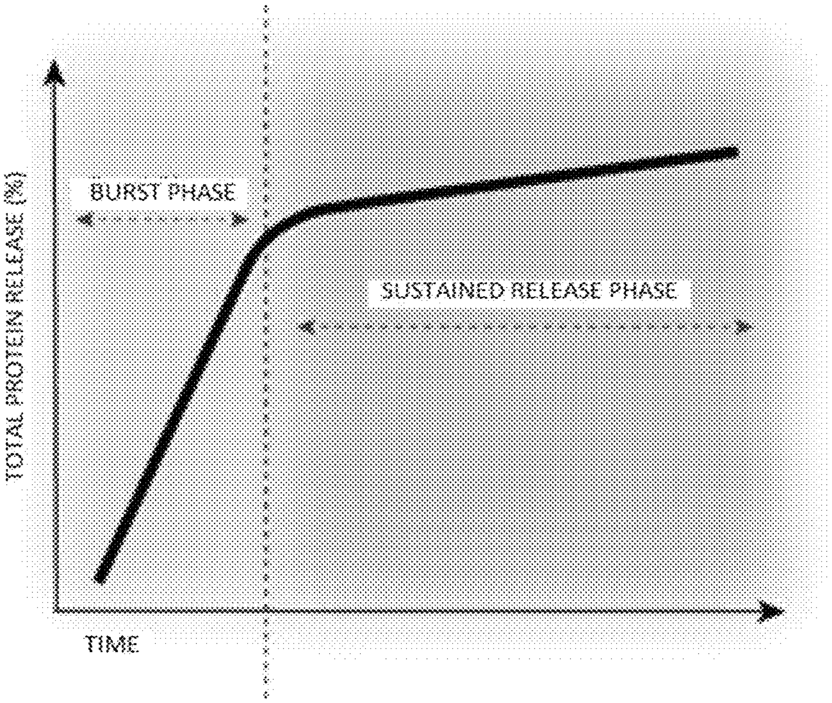
FIG. 1C shows a biphasic protein elution curve from PLGA nanospheres, due to initial release of adsorbed protein on the surface of the nanospheres, followed by controlled release of protein entrapped with the PLGA nanospheres.
Figure 1D:
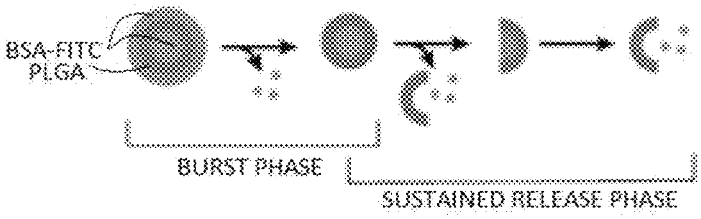
FIG. 1D shows the mechanism of biphasic protein release from PLGA nanospheres.

When the second emulsion can be formed, protein can become wound up in strands of the PLGA matrix polymer, which can coalesce and precipitate into a sphere as the organic solvent can be removed. During this process, protein can become both entrapped within the polymer matrix (FIG. 1A, where the protein can be fluorescein isothiocyanate-labeled bovine serum albumin [BSA-FITC]) and adsorbed to the outer surface (FIG. 1B), producing a characteristic biphasic elution curve shown in FIG. 1C. The burst phase, which can occur between baseline and two days, can be due to the adsorbed protein on the surface of the nanospheres being released upon resuspension in aqueous medium (FIG. 1D). The controlled release phase can be due to entrapped protein (FIG. 1D), and the protein can be released slowly over time as the PLGA hydrolyzes.

For purposes of comparison, the above process can be carried out using a buffered saline solution instead of a protein suspension, and adding this saline solution to the PLGA-containing oil phase to produce the first emulsion. Upon adding this first emulsion to a PVA aqueous phase, protein-free blank nanoparticles can be produced.

Blank nanospheres and IL-12-loaded PLGA nanospheres can be synthesized using the above techniques. The morphology of blank and protein-loaded PLGA nanospheres can be determined via scanning electron microscopy to be spherical in shape with a mean particle diameter of 50 nm to 500 nm, 100 to 250 nm, 100 to 150 nm, or 175 to 225 nm. In various embodiments, IL-12-loaded PLGA nanospheres can have a diameter of 100, 150, 200, 300, 400, 500, 600, 700, 800, 900, 1000 nm. Blank, i.e., protein-free nanospheres can have a diameter of 175 to 225 nm.

Zeta Potential

The zeta potentials of both blank and IL-12 loaded PLGA nanospheres were also determined in a deionized water medium. The zeta potential can be the potential difference between the dispersion medium and the stationary layer of fluid attached to the dispersed particle, and can range from −15 to −25 mV, respectively, following the introduction of 12.5-25 ug recombinant mouse IL-12 (rmIL-12) for protein loading during synthesis. As the magnitude of the zeta potential increases, the stability of the nanosphere dispersion can increase.

Encapsulation Efficiency

Protein can be eluted from the nanospheres in a nanosphere release buffer. The amount of IL-12 (percent) encapsulated and released (encapsulation efficiency, EE) by the nanospheres can be estimated using the area under the curve (AUC) of each elution profile, the particle concentration (PC; particles/mL), the total volume of synthesized particles (V, mL), and the total mass of IL-12 (mg) added during synthesis via the following equation;

$$EE = \left( \frac{\frac{AUC_{EP}}{100{,}000} + PC + V}{\text{Total } IL - 12 \text{ added}} \right) * 100\% \quad (1)$$

Elution can be measured by dispersing from 200 million particles/mL to 100 billion particles/mL, from 300 million particles/mL to 50 billion particles/mL, from 400 million particles/mL to 20 billion particles/mL, or from 500 million particles/mL to 1 billion particles/mL of protein-loaded PLGA nanospheres in a nanosphere release buffer, and analyzing the resulting dispersion for protein concentrations released over time. The protein concentrations can be bioactive. In the case of IL-12, the total amount of rmIL-12 eluted from the aforementioned particle concentrations can be determined by area under the curve (AUC) analysis to be from 1500 to 4,000 pg. The amount of IL-12 eluted per 100,000 nanospheres can be determined to be 0.3 to 0.45 pg/100,000 nanospheres, respectively, with the most efficient elution kinetics being obtained at a concentration of 750 million particles/mL and the least efficient elution kinetics being obtained at a concentration of 1 billion particles/mL for the particles made via the homogenization method. Based on equation (1), the average encapsulation efficiency (EE) was determined to range from 0.4% to 0.5%. The highest EE was obtained at a concentration of 750 million particles/mL.

To determine whether the synthesized nanospheres could indeed encapsulate protein and not merely adsorb it to the outer wall, PLGA nanospheres containing fluorescein isothiocyanate-labeled bovine serum albumin were synthesized. The resulted nanospheres were imaged via confocal microscopy to visualize the internal structure. Analysis confirmed that labeled BSA was successfully incorporated within the nanospheres.

Systemic Distribution

Figure 2:
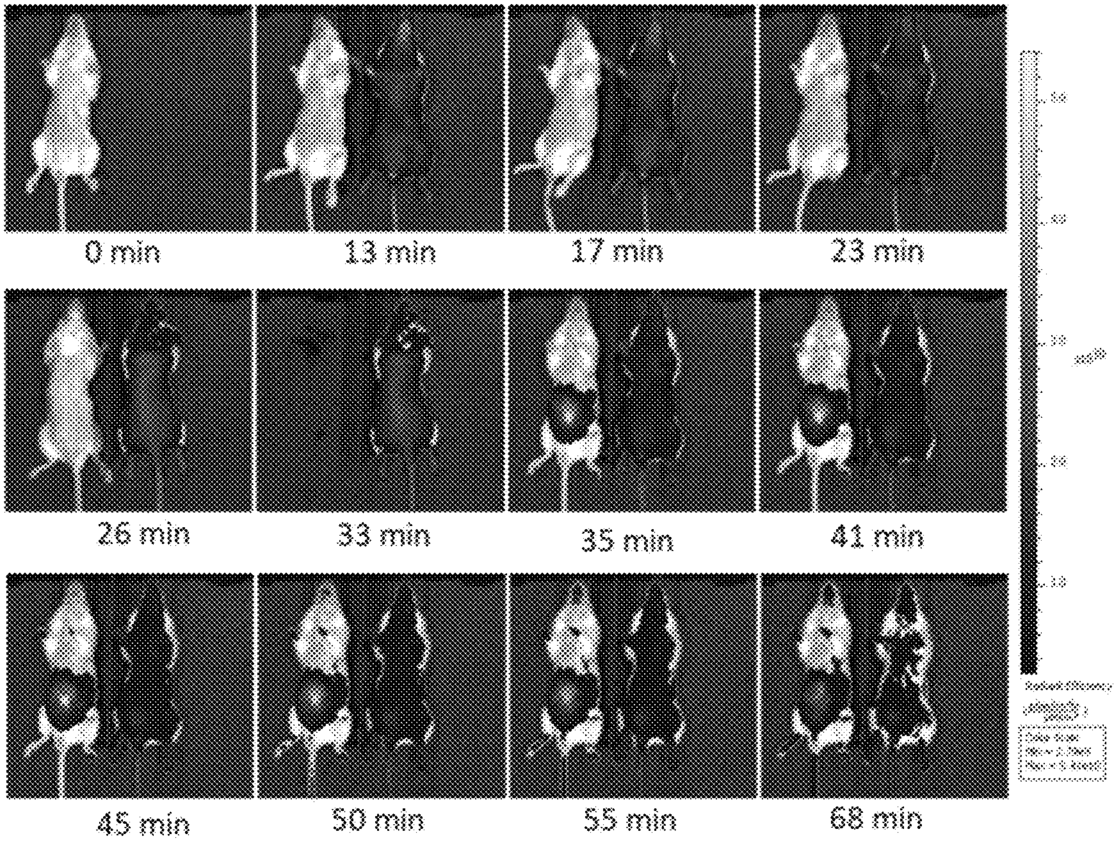
FIG. 2 shows fluorophore distribution over a 67-minute period in BALB/c mice inoculated with 1 mg/kg of Alexa Flour® 647-loaded nanospheres dissolved in sterile saline by either intraperitoneal (mouse on left) or intravenous (mouse on right) injection.

To determine whether the contents of PLGA nanospheres distribute systemically and without causing injury following various administration routes, PLGA nanospheres loaded with the fluorescent dye Alexa Fluor® 647 can be injected into female mice, either intravenously through the tail vein or intraperitoneally, and monitored via in vivo imaging systems. Both routes of administration can result in systemic distribution of nanosphere contents, as depicted in FIG. 2, without any signs of morbidity or mortality.

Water-Insoluble Payloads

Similar techniques can be used to encapsulate a water-insoluble free base or salt of a drug, or a water-insoluble dye or contrast agent, in a PLGA nanosphere, where the term "water-insoluble" means that the drug or salt is less soluble in water than in the organic solvent dissolving the PLGA polymer. Similar techniques can be used to encapsulate a soluble drug, dye, or contrast agent, where controlled release by a PLGA polymer is desired to provide a therapeutically safe and effective dose while avoiding toxic side effects from rapid initial release.

To create the oil phase, from 2.5% w/v to 17% w/v of PLGA can be dissolved in an organic solvent, e.g., a halogenated C1-C3 organic solvent; a C2-C3 nitrile solvent; a C2-C5 alkyl ester solvent; or a C3 to C5 ketone solvent. To create the aqueous phase of the emulsion, from 1% w/v to 3% w/v of polyvinyl alcohol (PVA) can be dissolved in an aqueous solvent, which can be water or a buffered saline solution, e.g., phosphate buffered saline.

Next, a water-insoluble free base or salt of a drug, a water-insoluble dye, or a contrast agent, can be suspended in an aqueous medium, and the resulting protein suspension can be added to the PLGA-containing oil phase, which can be subjected to rapid stirring or sonication to produce a first emulsion.

The first emulsion can then be added to the PVA aqueous phase with rapid stirring or sonication to produce a second emulsion. The organic solvent can then be evaporated from the second emulsion. PLGA nanoparticles containing the drug, dye, or contrast agent from the aqueous medium can be recovered by centrifugation, and can be lyophilized.

Additives

Various further modifications to the process for nanosphere preparation can increase encapsulation efficiency, and change the elution profile of the nanospheres. Preparation of nanospheres using a protein solution made by suspending 12.5 micrograms of IL-12 in 1.2 mL DPBS containing 1.5% w/v trehalose can produce nanospheres with delayed-release elution profile. The initial burst phase can be delayed to second day after the start of the elution study, but encapsulation efficiency can be decreased.

Preparation of nanospheres using a protein solution made by suspending 12.5 micrograms of IL-12 in 1.2 mL DPBS containing 2% w/v $Mg(OH)_2$ can produce nanospheres with decreased encapsulation efficiency.

Preparation of nanospheres using a protein solution made by suspending 12.5 micrograms of IL-12 in 1.2 mL DPBS containing 3% to 15%, 5% to 12%, 8% to 12%, or about 10% whole serum, serum albumin, fetal serum, or fetal serum albumin that is species specific to the patient can produce nanospheres with delayed release. The initial burst phase can be delayed to the second day after the start of the elution study, and encapsulation efficiency can be increased. If the IL-12 suspension is incubated with fetal serum for 24 hours prior to nanosphere preparation, the burst phase can be delayed to the third day after the start of the elution study. Further incubation with whole serum, serum albumin or fetal serum for 48 hours also prolongs the elution of the burst phase and increases encapsulation efficiency. For in vitro studies, any type of serum, serum albumin (including synthetically manufactured serum albumin), fetal serum, or fetal serum albumin can be used, e.g. fetal bovine serum or fetal murine serum. Alternatively, human serum can be used. For in vivo studies, where nanospheres can be administered to a human or non-human patient, selection of serum or serum albumin can be specific to the species to be treated. For treatment of cattle, nanospheres made by suspending IL-12 in DPBS containing fetal bovine serum can be used. For treatment of mice, nanospheres should be made with DPBS containing fetal murine serum. For treatment of humans, nanospheres can be made with DPBS containing human serum. Administering nanospheres treated with serum or fetal serum from one species to a different species can cause graft vs, host disease. Also, if using whole serum or collected native human albumin, a cross match process can be performed for each patient receiving these products, as can be the case for any blood product. In some cases, at least a portion of the therapeutic substance (e.g., IL-12) can elute from the composition (e.g., nanospheres) more than 24, 48, 72, 96, 120, 144, 168, 192, 216, 240, 264, 288, 312, 336 hours after placement of the composition in a solution. In some cases, least a portion of the therapeutic substance (e.g., IL-12) can elute from the composition (e.g., nanospheres) about 24 hr to about 48 hr, about 48 hr to about 72 hr, about 72 hr to about 192 hr, about 72 hr to about 168 hr, about 96 hr to about 168 hr, about 120 hr to about 168 hr, about 144 hr to about 192 hr after placement of the composition in a solution.

The presence of surfactants during nanosphere preparation can increase encapsulation efficiency. The surfactants can be incorporated into the PLGA-containing oil phase, or into the PVA/water phase. Suitable surfactants include oil-soluble sorbitan fatty acid esters (Span 20, Span 40, Span 60, and Span 80, for example), and/or water-soluble polyoxyethylene sorbitan fatty acid esters (Tween 20, Tween 40, Tween 60, and Tween 80, for example). In various embodiments, nanospheres can be prepared with a PLGA-containing oil phase containing 4% to 20% w/w of a Span surfactant, a PVA/water phase containing 2% to 10% w/v of a Tween surfactant, or both. For example, the oil phase can contain 4% to 20% w/w Span 60, 10% to 16% w/w Span 60, or about 14% w/w Span 60;

the PVA/water phase can contain 2% to 10% w/v Tween 80, 3% to 8% w/v Tween 80, or 4% to 6% w/v Tween 80; or the oil phase can contain 4% to 20% w/w Span 60 and the PVA/water phase can contain 2% to 10% w/v Tween 80.

The presence of both a surfactant and fetal serum can increase encapsulation efficiency. Preparation of nanospheres using a protein solution made by suspending 12.5 micrograms of IL-12 in 1.2 mL DPBS containing 10% fetal serum can produce nanospheres with an IL-12 encapsulation efficiency of between 2% and 10%, between 4% and 8%, or between 5% and 7%. Preparation of nanospheres using a protein solution made by suspending 12.5 micrograms of IL-12 in 1.2 mL DPBS containing 10% fetal serum which has been incubated in the DPBS for 24 hours can produce nanospheres with an IL-12 encapsulation efficiency of between 10% and 50%, between 20% and 45%, or between 30% and 40%. Preparation of nanospheres using a protein solution made by suspending 12.5 micrograms of IL-12 in 1.2 mL DPBS containing both 10% fetal serum and a surfactant can produce nanospheres with an IL-12 encapsulation efficiency of between 50% and 95%, between 60% and 85%, or between 70% and 80%. In various embodiments, use of a protein solution containing a cytokine, fetal serum, and a surfactant synergistically increases encapsulation efficiency of the cytokine in PLGA nanospheres.

Immunophenotyping

Various embodiments disclosed herein relate to a technique allowing a medical professional to systemically analyze the immune system of a patient from a blood draw or from two to three drops of blood obtained using a finger stick blood draw obtained using a lancet and Microtainer®. The blood draw can be done at home, in the office of a medical professional; in a clinic; or in a hospital.

In various embodiments, the blood draw can be done at home, in the office of a medical professional; in a clinic; or in a hospital. The blood draw can be analyzed at a testing site or a medical facility.

The blood sample can be analyzed for the level of an immunochemical naturally present in the body of the patient, and/or for the level of an immunomodulatory drug administered to the patient. The blood sample can be analyzed for the level of an immunochemical naturally present in the body of the patient, as a function of time, allowing a medical professional to observe the effect of a treatment regimen on the immunochemical levels. Blood draws can be taken and analyzed at regular intervals, allowing a medical professional to assess changes in the immune status, or immunophenotype, over the course of treatment.

Figure 11:
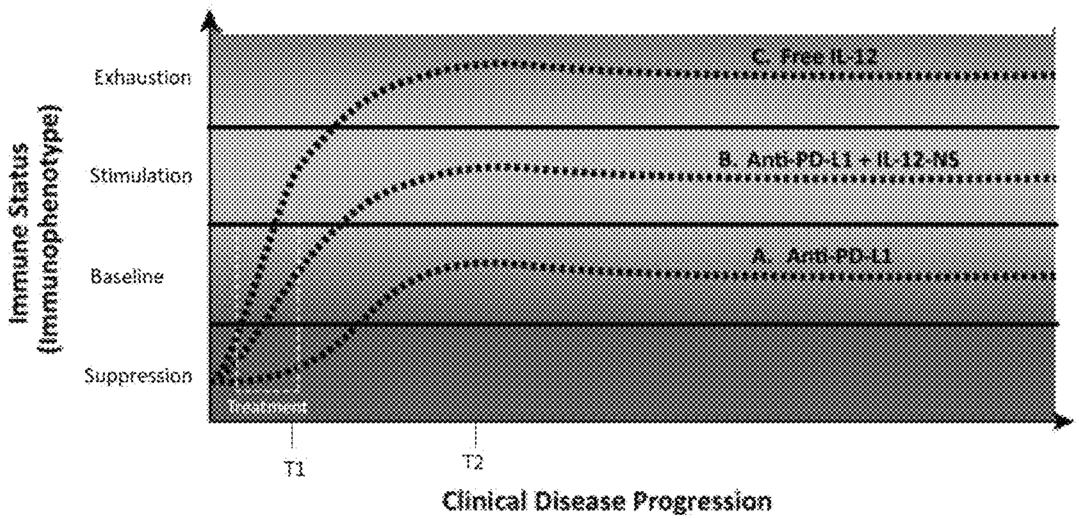
FIG. 11 shows application of IL-12 from PLGA nanospheres for the treatment of metastatic osteosarcoma.

Referring to FIG. 11, there are four major immunophenotypes under consideration:

Suppression, e.g., immunosuppression induced by cancer, an autoimmune disease, or an infection;

Baseline, e.g., the immune status of a disease-free subject;

Stimulation of the immune system above baseline levels; and

Exhaustion, a life-threatening state of immune system over-activation known as immune cell exhaustion (TCE), marked by characterized by lymphocyte anergy, systemic inflammatory response syndrome, and/or organ failure.

FIG. 11 shows the change in the immunophenotype of an osteosarcoma cancer patient during treatment with a variety of immunomodulating therapies. The patient's initial immunophenotype is Suppression, due to cancer-induced immunosuppression. Programmed cell death ligand 1 (PD-L1) is frequently expressed during osteosarcoma, so antibodies to PD-L1 (Anti-PD-L1) can be administered. See FIG. 11, line A. Interleukin-12 (IL-12) has been shown to inhibit tumor growth in osteosarcoma, so free IL-12 can be administered as an immunomodulator. See FIG. 11, line C.

At Time T1, Anti-PD-L1 appear to be ineffective in changing the patient's immunophenotype, while IL-12 appears to have changed the immunophenotype to Stimulation. However, at Time T2, as the treatment progresses, IL-12 causes toxic side effects, changing the patient's immunophenotype to Exhaustion. At Time T2, Anti-PD-L1 changes the patient's immunophenotype to baseline, combatting the cancer-induced immunosuppression without stimulating the immune system to fight the cancer.

As seen in FIG. 11, line B, combining Anti-PD-L1 with a low dose of IL-12 administered in PGLA nanospheres can stimulate the immune system to fight cancer without causing immune system over-activation. Thus, monitoring the immunophenotype over time allows a medical practitioner to adjust an immunomodulating therapy to provide immunostimulation without T-cell exhaustion.

Data relating to the immune response to a cancer therapy can be entered into a database. For example, referencing FIG. 11, the following information can be entered into the database for any given patient with a first disease which suppresses or overstimulates the immune system:

a) type of disease;
b) immunophenotype prior to treatment;
c) treatment administered for the first disease;
d) change in immunophenotype as a function of time;
e) clinical outcome;
f) medications taken by the patient for a second disease;
g) disease stage or disease level;
h) medical co-morbidities; and
i) age of the patient.

Changes in any one of those parameters can affect other parameters. For example, if a patient undergoing treatment for a first disease which affects the immune system is, after the initiation of treatment, diagnosed with a second disease, i.e., a medical co-morbidity, either a causative agent of the second disease or a symptom of the second disease can affect:

the clinical outcome of treatment of the first disease,
the change in the patient's immunophenotype over time,
the stage or level of the first disease, and/or
the efficacy of treatment administered for the first disease.

Similarly, a change in disease stage or disease level of the first disease, e.g., progression of a cancer from stage 2 to stage 3, can affect the patient's immunophenotype as a function of time, protocols for treatment of the first disease, and the clinical outcome of treatment of the first disease.

The database would thus include information on treatment of a variety of diseases with immunomodulating drugs, and allow predictions on how a particular patient presenting with that disease will respond to a given immunomodulating therapy.

Use of such a database allows a medical professional to predict the response of a patient's immune system to a given disease state, and to predict changes in the patient's immunophenotype over the course of a disease or treatment. The database will useful in the treatment, surveillance, and diagnosis of many diseases including cancer, autoimmune diseases, and infections. As immunomodulating agents become more common, such a database provides the ability to assess where the status of the immune system at a specific time in the pathogenesis of a disease, and to predict which immunomodulating treatments would be most effective in treating that disease.

Each blood sample obtained from a patient's blood draw or finger stick blood draw can be analyzed for the patient's immunophenotype at the time of the blood draw. The results of the analysis, together with information as to the patient's disease state and current treatment, if any, can be compared to data present in the database to develop a treatment plan which is most likely to effectively modulate the patient's immunophenotype. Blood draws can be taken and analyzed at regular intervals, allowing a medical professional to assess changes in the immune status, or immunophenotype, over the course of treatment. Data from the current patient can be added to the database, potentially improving assessments of other patients. This has massive commercial potential for analysis of a patient's blood with complex immunophenotyping, whether the analysis is for cancer, infection, or autoimmune diseases. The database that can be created with cross referencing of diseases with immunophenotyping will be a powerful tool to treat patients in the future. The database will be a living database that generates constantly updating information on immunophenotyping and status of treatment. Immunophenotyping of a patient's blood sample involves the ability to analyze and assess the data appropriately. This system will allow the appropriate dosing, treatment, and corrections to be made across several disease states. As the collection of data increases the growing database will also be able help direct medical professionals to diagnosis, treat, and dose immunotherapeutics in the broadest sense.

Although the various exemplary embodiments have been described in detail with particular reference to certain exemplary aspects thereof, it should be understood that the disclosure can be capable of other embodiments and its details can be capable of modifications in various obvious respects. As is readily apparent to those skilled in the art, variations and modifications can be affected while remaining within the spirit and scope of the disclosure. Accordingly, the foregoing disclosure, description, and figures are for illustrative purposes only and do not in any way limit the disclosure, which is defined only by the claims.

As discussed in Part F, the effect of IL-12-loaded PLGA nanospheres on metastasis in an immunocompetent K7M2 orthotopic murine model of osteosarcoma is explored. It was observed that nIL-12-treated mice, irrespective of dose, showed significantly better outcomes than untreated mice. Further, the decrease in metastatic rates was linked to increased NK cell percentages in peripheral blood at amputation. The observation that a particular component of the blood immunophenotype (NK cell percentage >8.21%) could potentially distinguish between complete and non-responders at such an early clinical time point (amputation) has obvious clinical implications. This provided a solid foundation for well-informed hypothesis generation. Indeed, the free rmIL-12 toxicity study highlighted IL-12-induced toxicities specific to BALB/c mice that could be surveyed alongside nIL-12 treatment, namely TCE status, PMN-MDSC myelocytosis, and NK cell depletion. This established that free rmIL-12 induces distinguishable changes in the BALB/c systemic immunopheneotype. Further, it can be shown that nIL-12 therapy can be efficacious against metastatic OS tumors and decreases the chances of disease relapse. Additionally, monitoring the NK cell percentages in peripheral blood can provide information about response to nIL-12 and outcome. This data support the fact that systemic immunophenotyping and experimental immunotherapies can be used hand-in-hand to generate efficacious immunotherapeutic regimens for metastatic OS.

While various embodiments of the disclosure have been shown and described herein, it will be obvious to those skilled in the art that such embodiments are provided by way of example only. Numerous variations, changes, and substitutions can occur to those skilled in the art without departing from the. It should be understood that various alternatives to the embodiments of the disclosure described herein can be employed.

EXAMPLES

In the following examples, dichloromethane (DCM, #320269), PLGA (Resomer RG 756 S, 75% lactide,

#719927), NaCl (#7647-14-5), and poly(vinyl alcohol) (#341584) were purchased from Sigma Aldrich (St. Louis, MO). Fluorescein isothiocyanate-labeled bovine serum albumin (BSA-FITC, #A23015), Penicillin-Streptomycin (Pen-Strep, 10,000 U/ml, #15140122) and Alexa Fluor® 647 carboxylic acid, tris(triethylammonium) salt were purchased from Thermofisher Scientific (Waltham, MA). Recombinant mouse IL-12 (p70, rmIL-12, #577008) and Mouse IL-12 ELISA MAX deluxe ELISA kits (#433606) were purchased from Biolegend (San Diego, CA).

Gibco Fetal Bovine Serum Qualified Heat Inactivated US Origin (HI-FBS, #MT35011CV) and Dulbecco's Phosphate-Buffered Salt Solution 1× (DPBS, #21031CV) were purchased from Fisher Scientific (Pittsburgh, PA).

Female BALB/c mice (6-8 weeks of age) (#000651) were purchased from the Jackson Laboratory (Bar Harbor, ME).

Part A. IL-12 Stability Studies.

Example 1. Stability of IL-12 in Acidic and Basic Solutions

To determine if IL-12 could handle the acidic nanoenvironment of a PLGA nanosphere, the recovery of bioactive recombinant mouse IL-12 following a three hour exposure to solutions of varying pH was tested. Specifically, IL-12 was incubated for 3 hours in a solution of pH 1, a solution of pH 3, a solution of pH 7.4, a solution of pH 11, and a solution of pH 13. The results are shown in Table 1. The percentage of active IL-12 recovered, relative to an initial concentration, was determined using enzyme-linked immunosorbent assay (ELISA) to determine the amount of protein in its native, and hence biologically-active, conformation.

TABLE 1

IL-12 stability as a function of pH.

| pH | IL-12 Recovery (%) |
|---|---|
| 1 | 0% ± 0% |
| 3 | 39.7% ± 8.44% |
| 7.4 | 100% ± 0% |
| 11 | 96.6% ± 6.08% |
| 13 | 0% ± 0% |

As seen in Table 1, IL-12 has good stability at a pH value of 7.4 to 11, and can be subject to denaturation outside this range.

Example 2. Stability of IL-12 in Organic Solvents

The double emulsion method of synthesizing PLGA nanospheres can involve dissolving the PLGA in an organic solvent. Therefore, the stability of IL-12 was tested in several aprotic solvents of varying polarity. The organic solvents tested, in order of increasing hydrophilicity, were dichloromethane (DCM), ethyl acetate (EA), and acetone (AC). While DCM dissolves PLGA well, it is also the most hydrophobic and hence can have the greatest effect on the biological activity of IL-12. PLGA can be poorly soluble in acetone, but this solvent is the most polar and therefore can affect the bioactivity of IL-12 the least.

IL-12 was added to a 1:1 solution of solvent and phosphate-buffered salt solution, and stirred to completely remove the organic solvent; the remaining bioactive IL-12 concentrations were then determined using ELISA and expressed as a percentage, relative to an initial concentration. The results are shown in Table 2. Interestingly, AC had the most detrimental effect on the protein with only 43% (SE=1.06%) recovered, while EA showed the highest recovery at 63% (SE=0.77%); DCM left approximately half of the protein in its native form (49%, SE=0.55).

TABLE 2

IL-12 stability as a function of organic solvent.

| Solvent | IL-12 Recovery (%) |
|---|---|
| DCM | 49% ± 0.55% |
| EA | 63% ± 0.77% |
| AC | 43% ± 1.06% |

Unless otherwise indicated, DCM was used to create nanosphere batches in further examples. Although use of DCM as a solvent led to reduced protein recovery, when compared to ethyl acetate, DCM dissolves PLGA better and results in better nanosphere morphology.

Example 3. Stability of IL-12 Upon Sonication

To form emulsions when synthesizing PLGA nanospheres, IL-12 can be subjected to sonication twice. Ultrasonication during nanosphere preparation can result in more uniform and smaller nanospheres. However, sensitive proteins like IL-12 become denatured when exposed to intense agitation.

Figure 3:
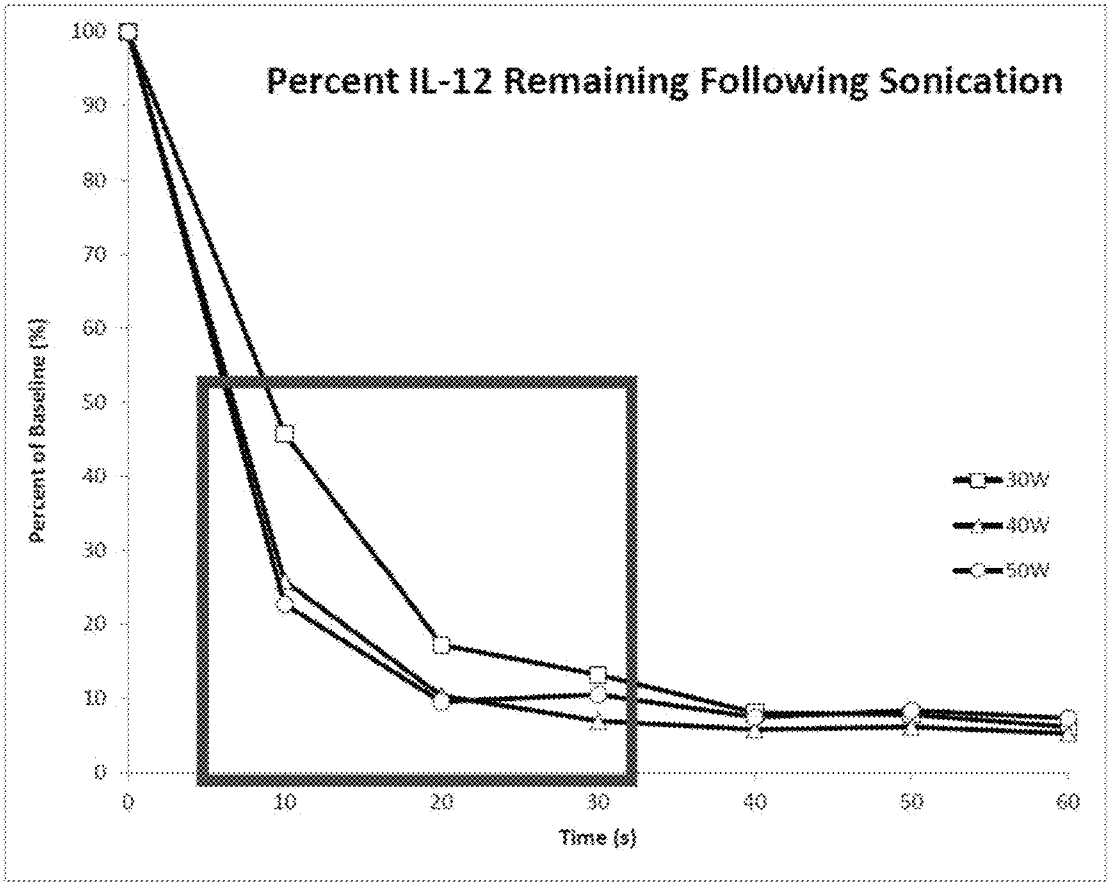
FIG. 3 shows the effect of sonication on IL-12, where IL-12 was ultrasonicated at three different wattages for 10, 20, 30, 40, or 60 seconds.
Figure 4A:
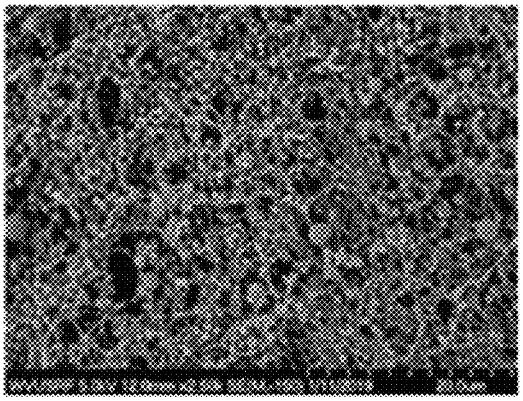
FIGS. 4A and 4B show scanning electron microscopy (SEM) images of unloaded (blank) poly(lactide-co-glycolide) acid (PLGA) nanospheres lyophilized without 25 mM trehalose at 11,000× (FIG. 3*a*) and 13,000× (FIG. 3*b*), respectively.
Figure 4B:
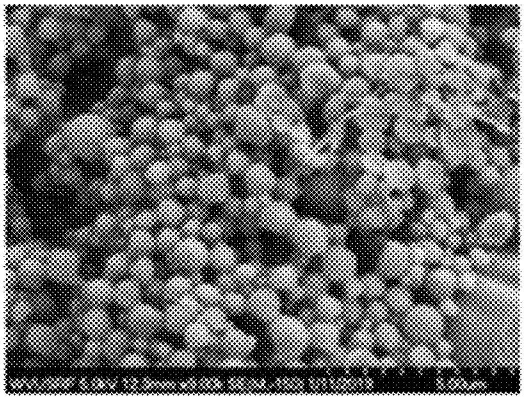
Figure 4C:
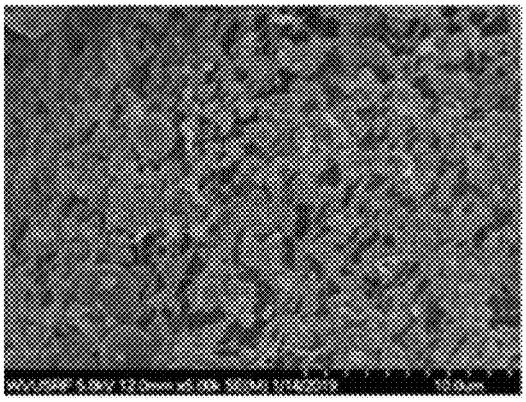
FIG. 4C shows scanning electron microscopy (SEM) images of unloaded (blank) PLGA nanospheres lyophilized with 25 mM trehalose at 5,000× magnification.

Therefore, various sonication wattages and times were tested to determine suitable conditions for IL-12-loaded PLGA nanosphere synthesis. IL-12 was suspended in a phosphate-buffered salt solution, and sonicated at 30 Watts, 40 Watts, or 50 Watts. The duration of sonication was 10, 20, 30, 40, or 60 seconds and compared to baseline. The bioactive IL-12 concentrations remaining after sonication were then determined using ELISA and expressed as a percentage, relative to an initial concentration. IL-12 was found to be more sensitive to time than wattage, as protein recovery past 30 seconds was less than 10% for all wattages, as seen in FIG. 3. The scanning electron microscopy (SEM) images of various IL-12-loaded batches are shown in FIGS. 4A to 4C. The box in FIG. 3 indicates the combination of times/wattages that recover the most protein, i.e., sonication at 30 Watts to 50 Watts for 5 to 30 sec.

Unless otherwise indicated, nanospheres made by sonication in subsequent examples were prepared using:

Sonication at 30 Watts for 10 to 20 sec;

Sonication at 40 Watts for 10 to 15 sec; or

Sonication at 50 Watts for 10 to 15 sec.

Part B. Studies on PLGA Nanospheres.

Example 4. Synthesis of PLGA Nanospheres

To create an oil phase, 800 mg of PLGA was dissolved in 32 ml DCM at room temperature for two hours using a magnetic stir bar at 500 RPM.

To create an aqueous phase of the emulsion, 2400 mg PVA and 96 mg NaCl were dissolved in 120 ml deionized water and microwaved for 10 second bursts in a standard kitchen microwave on setting HIGH until clear. The aqueous phase was then cooled on ice.

The first emulsion (w1) was made by suspending a material to be encapsulated in 1.2 mL DPBS and added the resulting suspension to the oil phase, which was stirred at 17,500 RPM using a tissue homogenizer for 6 minutes. The stirring was performed on ice. As a control, blank particles were made with no encapsulation material suspended in the DPBS.

The second emulsion (w2) was formed by slowly pouring the first emulsion into 120 ml of the aqueous phase. During addition of the first emulsion, the aqueous phase was stirred with the tissue homogenizer at 17,500 RPM. Following addition of the first emulsion, stirring was continued for a total of 8 minutes. The resulting suspension was then stirred for 16 hours with a magnetic stir bar at 750 RPM to evaporate the organic solvent.

Once the solvent was evaporated, the resulting solution was centrifuged at 3500 RPM three times; following each centrifugation step, a pellet of nanospheres can be recovered and resuspended, while the supernatant produced during centrifugation can be collected and stored on ice. The nanospheres were then washed twice via ultracentrifugation at 20,000 RPM for 40 minutes at 4 degrees Celsius, flash-frozen in liquid nitrogen, and stored at −20 degrees Celsius.

The nanospheres can then be lyophilized under vacuum to remove water from the nanospheres.

Figure 5A:
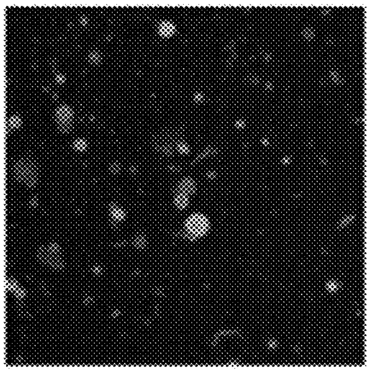
FIG. 5A shows PLGA nanospheres loaded with FITC-conjugated bovine serum albumin visualized for protein incorporation via confocal microscopy.

The properties of nanospheres obtained are summarized in Table 3. Nanospheres containing FITC-labeled BSA, described in Table 3, were imaged via confocal microscopy to visualize the internal structure. As shown in FIG. 5A, Z-stacking analysis confirmed that FITC-labeled BSA was successfully incorporated within the nanospheres.

Figure 5B:
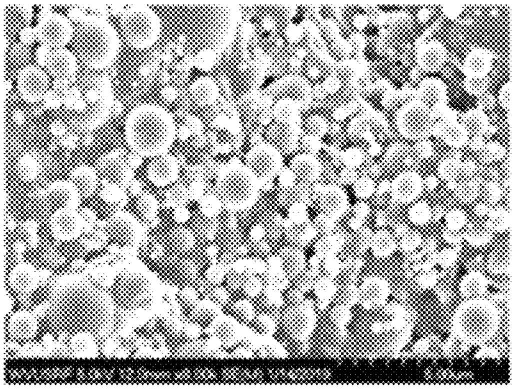
FIGS. 5B and 5C show scanning electron microscopy (SEM) images of lyophilized recombinant mouse IL-12-loaded PLGA nanospheres at 8,000× and 25,000× magnification, respectively.
Figure 5C:
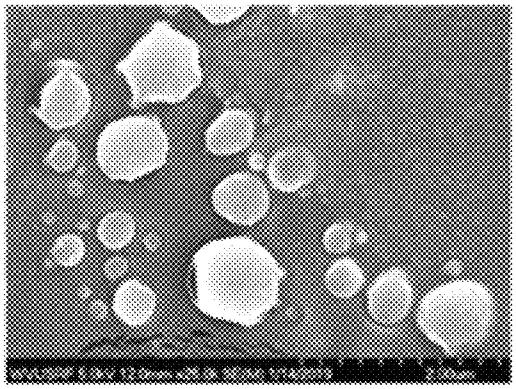
Figure 6A:
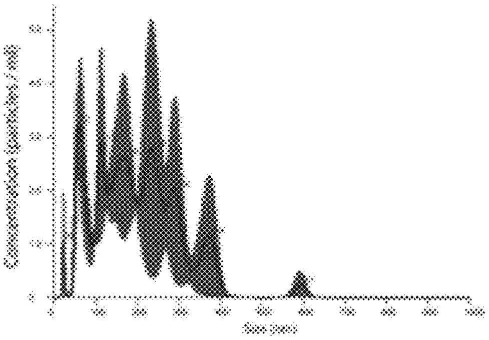
FIGS. 6A and 6B show size distribution analyses of unloaded (blank) PLGA acid nanospheres and recombinant mouse IL-12 (IL-12)-loaded PLGA nanospheres run at 1:50 and 1:14 dilution factors in water at 25 degrees Celsius, respectively.
Figure 6B:
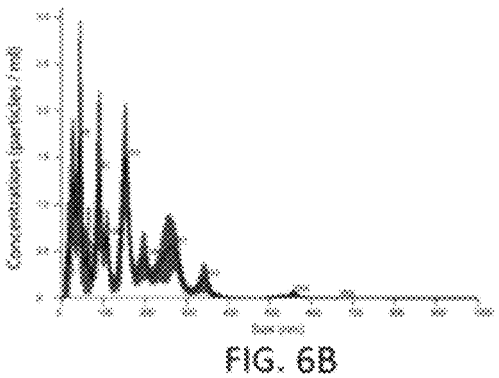
Figure 6C:
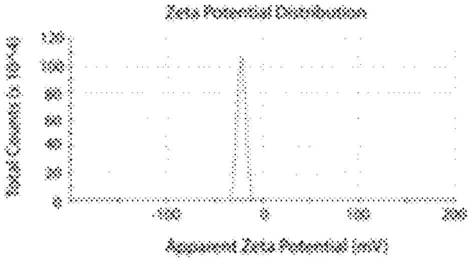
FIGS. 6C and 6D show zeta potential distributions for unloaded blank and IL-12-loaded PLGA nanospheres at a 1:50 dilution factor in water at 25 degrees Celsius, respectively.
Figure 6D:
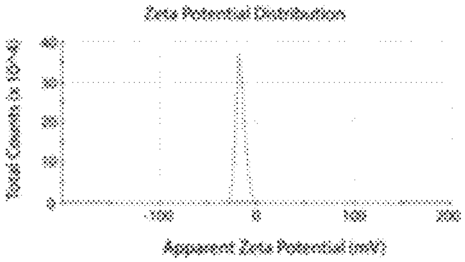

The morphology of both blank (FIGS. 4A to 4C) and IL-12 loaded (FIGS. 5B and 5C) PLGA nanospheres was determined via scanning electron microscopy (SEM) to be spherical in shape, with a mean particle diameter of 201.7±6.7 nm (FIG. 6A) and 138.1±10.8 nm (FIG. 6B), respectively. Zeta potentials of both blank and loaded PLGA nanospheres were also determined, with a decrease in the magnitude of the voltage from −21.3±0.808 mV (FIG. 6C) to −15.1±1.249 mV (FIG. 6D), respectively.

Nanospheres containing the Alexa 647 dye and fluorescein isothiocyanate-labeled bovine serum albumin (BSA-FITC) were also successfully prepared using the above procedure.

TABLE 3

Nanosphere Properties.

| Encapsulation Material | Amount/ 1.2 mL DPBS | Nanosphere Diameter (nm) | Zeta Potential (mV) | Nanosphere Concentration (Particles/mL) |
|---|---|---|---|---|
| Nothing | — | 201.7 ± 6.7 | −21.3 ± 0.81 | $6.49 \times 10^9$ ± $6.19 \times 10^8$ |
| Alexa 647 | 5 mg | — | — | — |
| BSA-FITC | 5 mg | — | — | — |
| IL-12 | 0.025 mg | 138.1 ± 10.8 | −15.1 ± 1.25 | $1.66 \times 10^9$ ± $4.45 \times 10^8$ |

Example 5. Nanosphere IL-12 Elution Profile

PLGA nanospheres encapsulating IL-12 were obtained by the process of Example 4. Three different concentrations (500 million particles/mL, 750 million particles/mL, and 1 billion particles/mL) of IL-12-loaded PLGA nanospheres were prepared in 500 μl of nanosphere release buffer (NRB, 10% HI-FBS and 100 units/ml Pen-Strep in DPBS). The suspensions were then centrifuged for 15 minutes at 4° C., to pellet the nanospheres, after which a 250 μl aliquot of the supernatant was removed and stored at 4° C. While on ice, 250 μl NRB was then added to the pellet to bring the total volume back up to 500 μl, which was resuspended and incubated at 37° C. with constant agitation (750 RPM) for 24 hours. This process was repeated for a total of 12 samples over 12 days (1 time point sample/24 hours). Each aliquot was stored at 4 degrees Celsius for at least 24 hours to equilibrate with the release buffer before determining IL-12 concentration via ELISA. The aliquots were analyzed via ELISA for bioactive IL-12 concentrations released over time.

The total amount of IL-12 eluted was determined by ELISA and subsequent area under the curve (AUC) analysis to be:

1907.66±162.00 pg at a nanosphere concentration of 500 million particles/mL, 3329.77±162.67 pg at a nanosphere concentration of 750 million particles/mL, and 3415.64±848.94 pg at a nanosphere concentration of 1 billion particles/mL.

The amount of IL-12 eluted per 100,000 nanospheres was determined to be:

0.3815±0.03240 pg/100,000 particles at a nanosphere concentration of 500 million particles/mL, 0.4440±0.02169 pg/100,000 particles at a nanosphere concentration of 750 million particles/mL, and 0.3416±0.08489 pg/100,000 particles at a nanosphere concentration of 1 billion particles/mL.

The 750 million particles/mL sample reported the most efficient elution kinetics of the three concentrations tested.

Figure 7A:
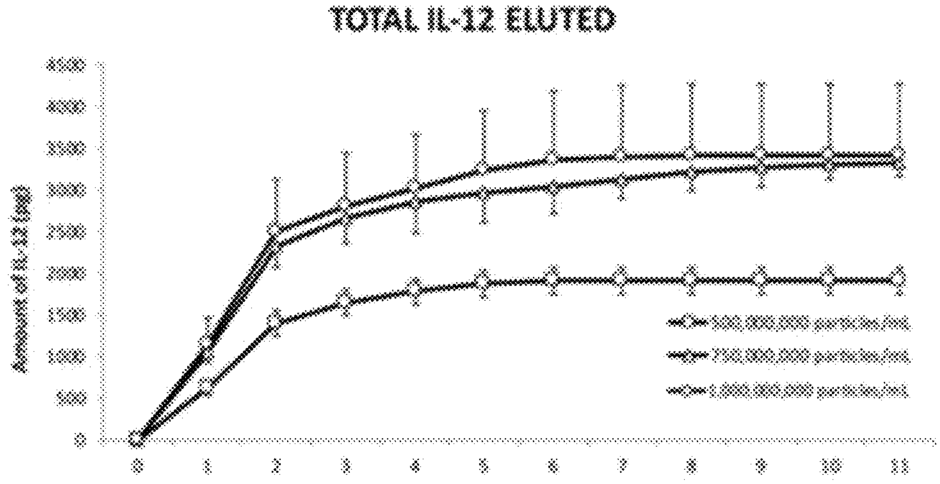
FIGS. 7A and 7B shows the estimated total amount of protein eluted over time from recombinant mouse IL-12-loaded PLGA nanospheres in terms of total protein (FIG. 7A) and protein per 100,000 particles (FIG. 7B).
Figure 7B:
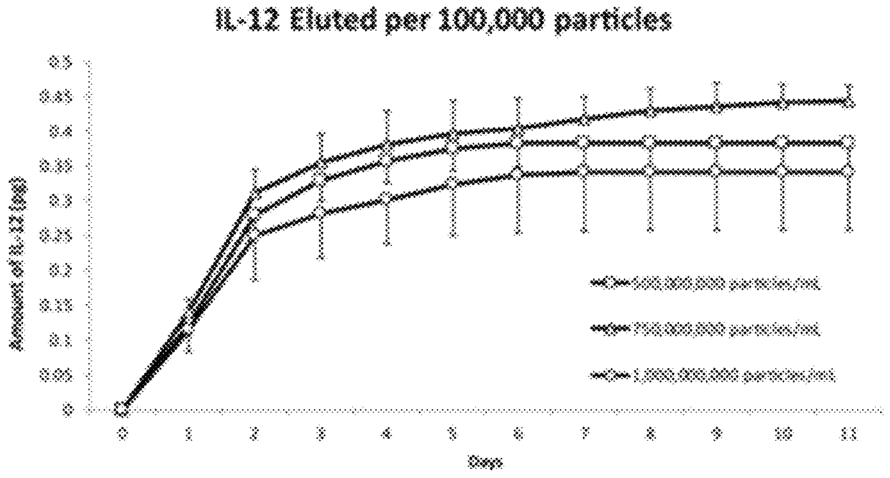

As seen in FIG. 7A, IL-12 concentration eluted as a function of time at a nanosphere concentration of 750 million particles/mL is significantly greater than IL-12 concentration eluted as a function of time at a nanosphere concentration of 500 million particles/mL. However, there can be little difference between IL-12 elution as a function of time at a nanosphere concentration of 750 million particles/mL and IL-12 elution as a function of time at a nanosphere concentration of 1 billion particles/mL. Also as seen in FIG. 7A, IL-12 nanoparticles show a biphasic elution profile, with a burst phase lasting about 2 days and a sustained release phase lasting about from about day 3 to day 11. Moreover, the total amount of IL-12 eluted over time at a nanosphere concentration of 750 million particles/mL can be about 75% greater than the total amount of IL-12 eluted at a nanosphere concentration of 500 million particles/mL. However, the total amount of IL-12 eluted at a nanosphere concentration of 1 billion particles/mL can be only about 2.6% greater than the total amount of IL-12 eluted at a concentration of 750 million particles/mL. As seen in FIG. 7B. IL-12 concentration eluted per 100,000 particles, as a function of time, can be greater at a nanosphere concentration of 750 million particles/mL than at a concentration of either 500,000 particles/mL or 1 billion particles/mL.

Figure 7C:
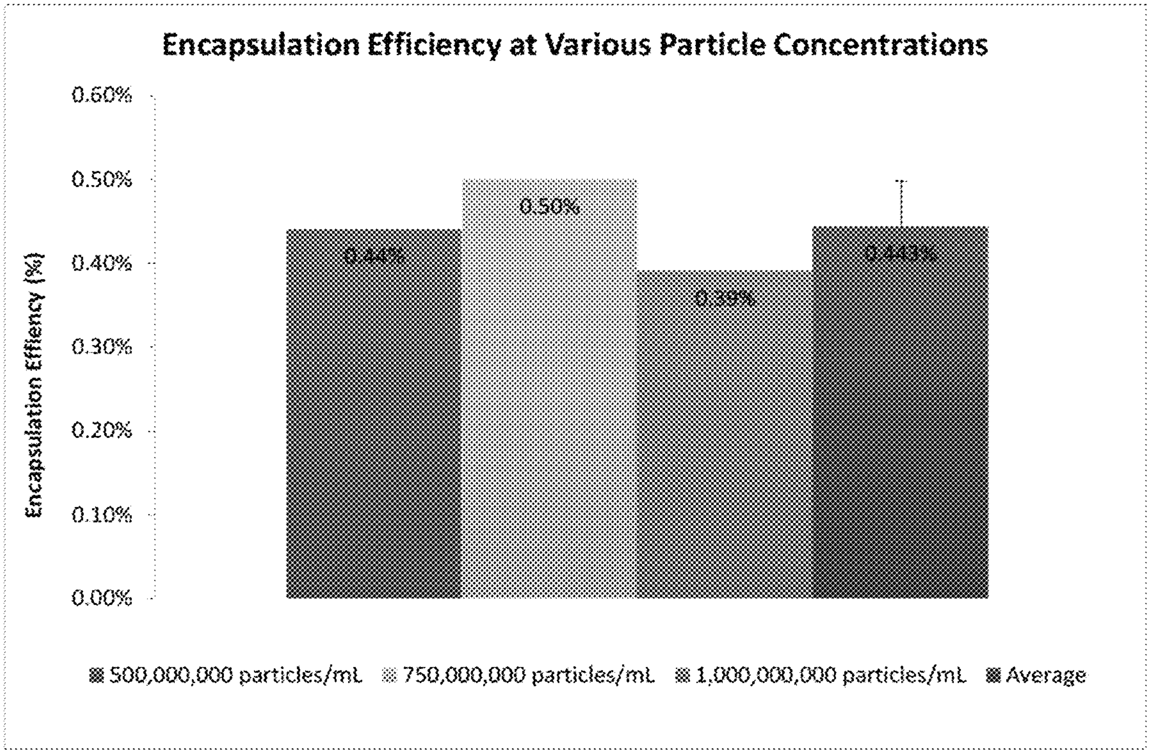
FIG. 7C shows the encapsulation efficiency (EE) of recombinant mouse IL-12-loaded nanospheres calculated using the area under the curve (AUCs) of each elution profile for three different particle concentrations (500 million particles/mL, 750 million particles/mL, and 1 billion particles/mL).

As shown in FIG. 7C, the encapsulation efficiency (EE) of recombinant mouse IL-12 (rmIL-12)-loaded nanospheres was calculated using the area under the curve (AUCs) of each elution profile for the three different particle concentrations investigated, using Equation 1. The amount of IL-12 eluted per 100,000 nanospheres was determined to be 0.44% at a nanosphere concentration of 500 million particles/mL, 0.50% at a nanosphere concentration of 750 million particles/mL, and 0.39% at a nanosphere concentration of 1 billion particles/mL. The average encapsulation efficiency (EE) can be 0.443%±0.0551%. Due to differing elution kinetics from the tested concentrations, EE was reported for all three concentrations and subsequently averaged to reflect overall EE.

Based on the above data, increasing the nanosphere concentration above 750 million particles/mL cannot offer a significant increase in the elution profile of the drug, possibly due to reduced encapsulation efficiency at high particle concentrations. However, this can be due to the constraints of eluting particles in vitro in a small volume (500 μL) of elution solvent. Elution in a larger volume, e.g., a larger volume of an in vitro elution solvent or an in vivo blood supply, can provide an increased elution profile as the nanosphere concentration increases above 750 million particles/mL.

Example 6. In Vivo Alexa 647-Loaded PLGA Nanosphere Substrate Biodistribution

PLGA nanospheres loaded with the fluorescent dye Alexa 647, described in Table 1, were injected into female BALB/c mice. In a first group of mice, the dye-loaded PLGA nanospheres were injected intravenously through the tail vein. In a second group of mice, the dye-loaded PLGA nanospheres were injected intraperitoneally. Dye distribution was monitored via IVIS imaging over a 76-minute period. At 35 minutes post-injection, both routes of administration resulted in systemic distribution of nanosphere contents, as depicted in FIG. 2. Intravenous injection resulted in generalized distribution of labeled dye through the body of the subject mouse. Intraperitoneal injection resulted in localized distribution of labeled dye within the abdominal cavity of the subject mouse, with the most intense distribution of the dye within the peritoneal cavity. Distribution occurred without any signs of morbidity or mortality.

Part C. Studies on PLGA Nanospheres with Sonication.

Example 7. Synthesis of PLGA Nanospheres with Sonication

To create an oil phase, 250 mg of PLGA was dissolved in 1.51 ml DCM at room temperature. 1 g PVA was dissolved in 100 ml deionized water to create an aqueous phase. The aqueous phase was then cooled on ice. The first emulsion (w1) was made by suspending 12.5 micrograms of IL-12 in about 20±6 microliters DPBS and adding the resulting suspension to the oil phase with sonication at 30 to 50 Watts for 10 to 20 sec.

The second emulsion (w2) was formed by slowly adding the first emulsion into 5 ml of the aqueous phase. During addition of the first emulsion, the aqueous phase was subjected to sonication at 30 to 50 Watts for 10 to 30 sec. The resulting suspension was then stirred for 3 hours with a magnetic stir bar at 1,000 RPM to evaporate the organic solvent.

Once the solvent was evaporated, nanospheres were recovered from the resulting solution via three ultracentrifugation treatments at 10,000 g for 15 minutes at 4 degrees Celsius, flash-frozen in liquid nitrogen, and stored at −20 degrees Celsius.

The nanospheres can then be lyophilized under vacuum to remove water from the nanospheres.

Figure 8A:
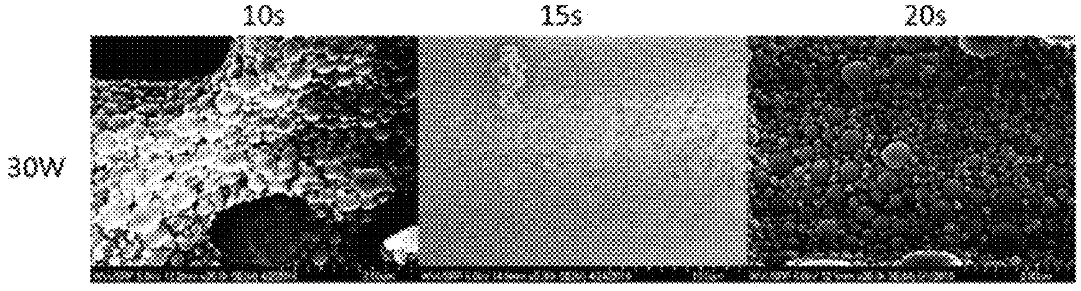
FIGS. 8A to 8C show IL-12-loaded nanospheres prepared using sonication under varying conditions of sonication power and sonication time.

FIG. 8A shows IL-12-loaded nanospheres prepared using sonication at a sonication power of 30 Watts and a sonication time ranging from 10 sec to 20 sec (Batches 30W10S, 30W15S, and 30W20S of Table 2).

Figure 8B:
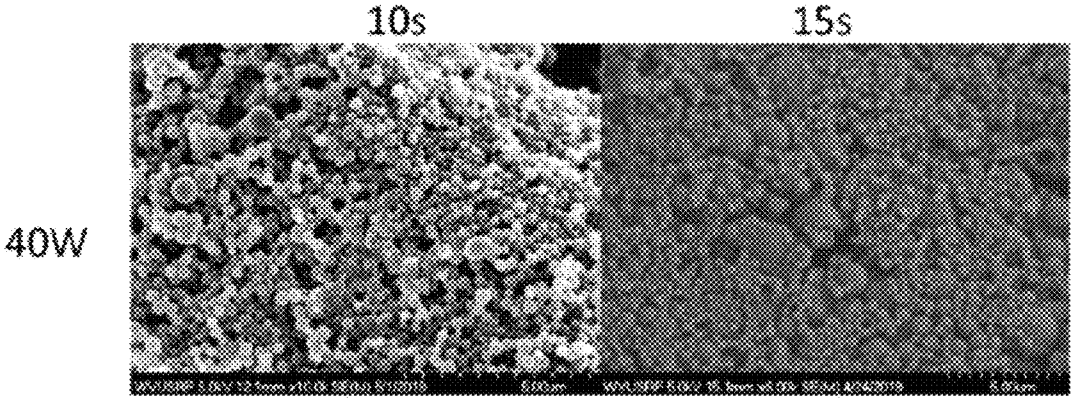

FIG. 8B shows IL-12-loaded nanospheres prepared using sonication at a sonication power of 40 Watts and a sonication time ranging from 10 sec to 15 sec (Batches 40W10S and 40W15S of Table 2).

Figure 8C:
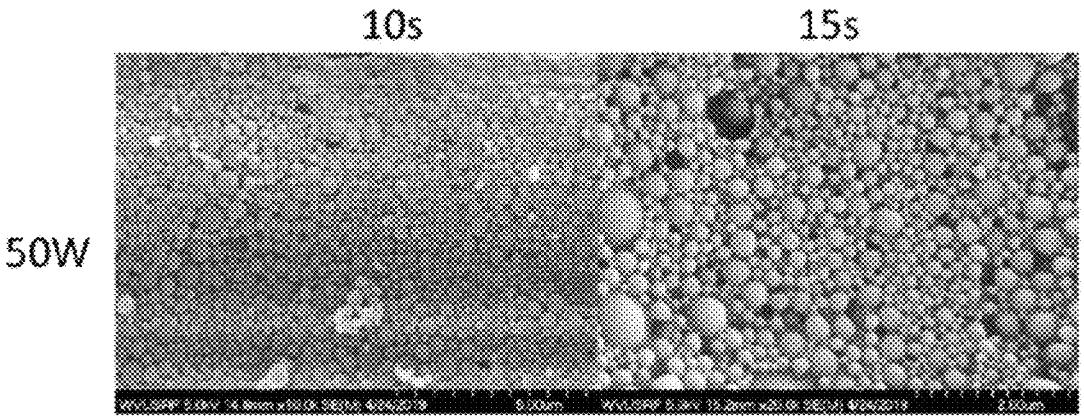

FIG. 8C shows IL-12-loaded nanospheres prepared using sonication at a sonication power of 50 Watts and a sonication time ranging from 10 sec to 15 sec (Batches 50W10S and 50W15S of Table 2).

As seen in Table 4, sonication with 30 Watts to 50 Watts power for 10 to 20 sec generally produces IL-12 loaded PLGA nanospheres with an encapsulation efficiency of about 5% to about 10%, and a zeta potential of between −30 and −40 mV.

TABLE 4

Impact of Sonication Conditions on Nanosphere Properties

| Sonication Power | Particle Batch | Sonication Time | Encapsulation Efficiency (%) | Zeta Potential (mV) |
|---|---|---|---|---|
| 30 W | 30W10S | 10 sec | 9.67 ± 4.25 | −36.15 ± 2.25 |
| | 30W15S | 15 sec | 7.60 ± 3.45 | −38.15 ± 4.75 |
| | 30W20S | 20 sec | 4.84 ± 0.80 | −31.75 ± 6.35 |
| 40 W | 40W10S | 10 sec | 6.23 ± 1.29 | −31.55 ± 8.35 |
| | 40W15S | 15 sec | 6.92 ± 0.44 | −33.55 ± 7.35 |
| 50 W | 50W10S | 10 sec | 8.80 ± 1.88 | −36.35 ± 2.85 |
| | 50W15S | 15 sec | 5.20 ± 3.10 | −35.50 ± 4.90 |

Example 8. Elution of PLGA Nanospheres Prepared with Sonication

The IL-12-loaded nanospheres shown in Table 2 were tested for elution characteristics by the procedure of Example 5. Protein concentration per day was determined by ELISA, and the total protein released was determined using the area under the raw elution curve.

Figure 9:
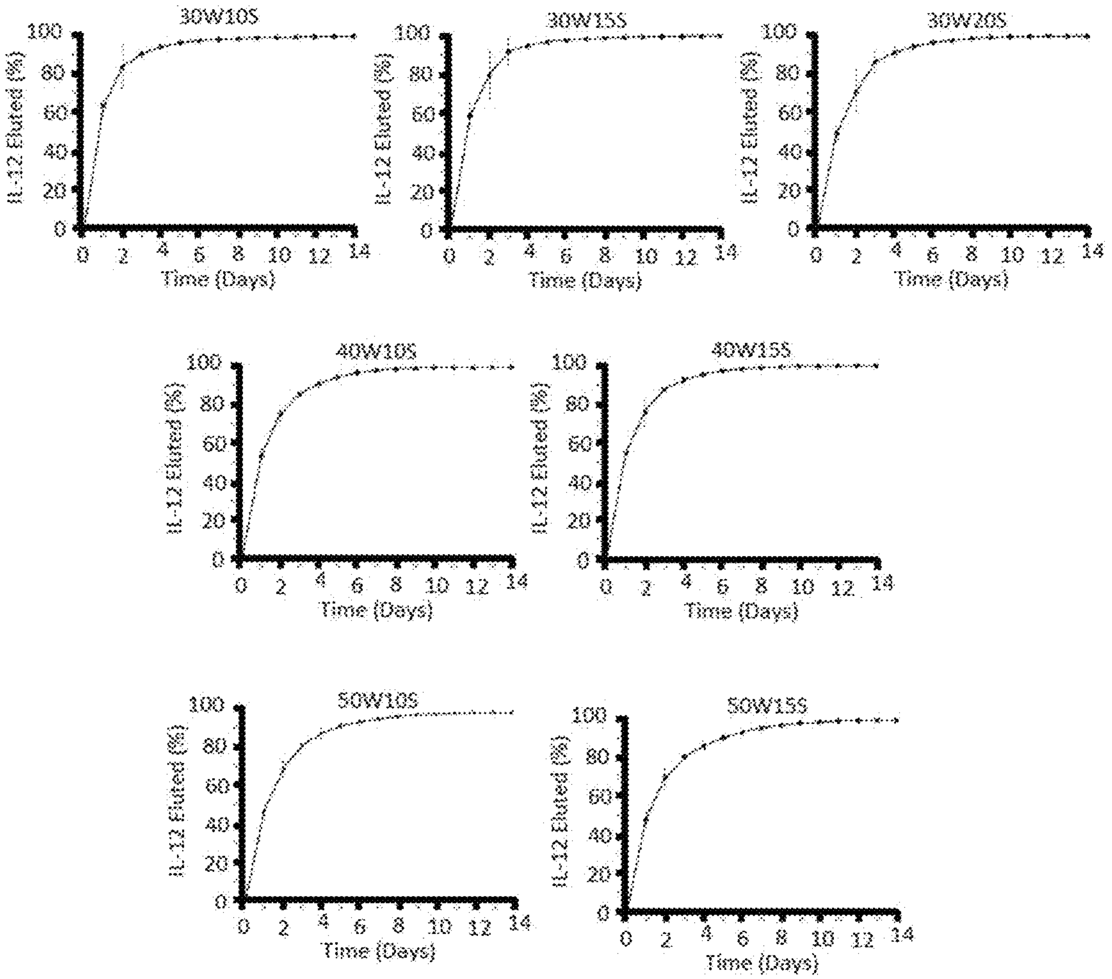
FIG. 9 shows the elution profiles of IL-12 from nanospheres prepared using sonication under varying conditions of sonication power and sonication time.

Elution curves obtained by the above procedure are shown in FIG. 9. The elution curve for each batch of Table 2 shows a biphasic curve with an initial burst phase and a sustained release phase. The burst phase can be due to the adsorbed protein on the surface of the nanospheres being released upon resuspension in aqueous medium, while the controlled release phase can be due to protein entrapped within the PLGA matrix. As seen in FIG. 8, for a constant sonication period, e.g., 10 sec., the initial rate of drug release during the burst phase decreases as the sonication power increases. In a batch sonicated for 10 sec at 30 W power (30W10S), between 60% and 65% of the IL-12 can be eluted within one day. In a batch sonicated for 10 sec at 50 W power (50W10S), less than 50% of the IL-12 can be eluted within one day. This suggests that the percentage of protein within the PLGA matrix in the nanosphere core increases as the sonication power increases.

Part D. Impact of Stirring Speed on PLGA Nanospheres.

Example 9

To create an oil phase, 800 mg of PLGA was dissolved in 32 ml DCM at room temperature for two hours using a magnetic stir bar at 500 RPM.

To create an aqueous phase of the emulsion, 2400 mg PVA and 96 mg NaCl were dissolved in 120 ml deionized water and microwaved for 10 second bursts in a standard kitchen microwave on setting HIGH until clear. The aqueous phase was then cooled on ice.

An IL-12 suspension was made by suspending 25 micrograms of IL-12 in 1.2 mL DPBS.

Nanospheres were prepared as described in Example 4.

To observe the impact of stirring speed on encapsulation efficiency of IL-12 in a PLGA nanosphere, and elution profile of IL-12 from PLGA nanospheres, stirring during preparation of the first and second emulsions was done at speeds of 13,125 RPM; 15,312 RPM; 17,500 RPM; 19,688 RPM; 21,875 RPM; 24,063 RPM; and 26,250 RPM. Encapsulation efficiency as a function of agitation speed is shown in Table 5.

TABLE 5

Encapsulation Efficiency as a function of stirring speed.

| Setting on Tissue Homogenizer | Agitation Speed (RPM) | Encapsulation Efficiency (%) |
|---|---|---|
| 3 | 13,125 | 0.68 |
| 3.5 | 15,312 | 0.50 |
| 4 | 17,500 | 2.06 |
| 4.5 | 19,688 | 0.94 |
| 5 | 21,875 | 0.70 |
| 5.5 | 24,063 | 0.50 |
| 6 | 26,250 | 0.15 |

Figure 10:
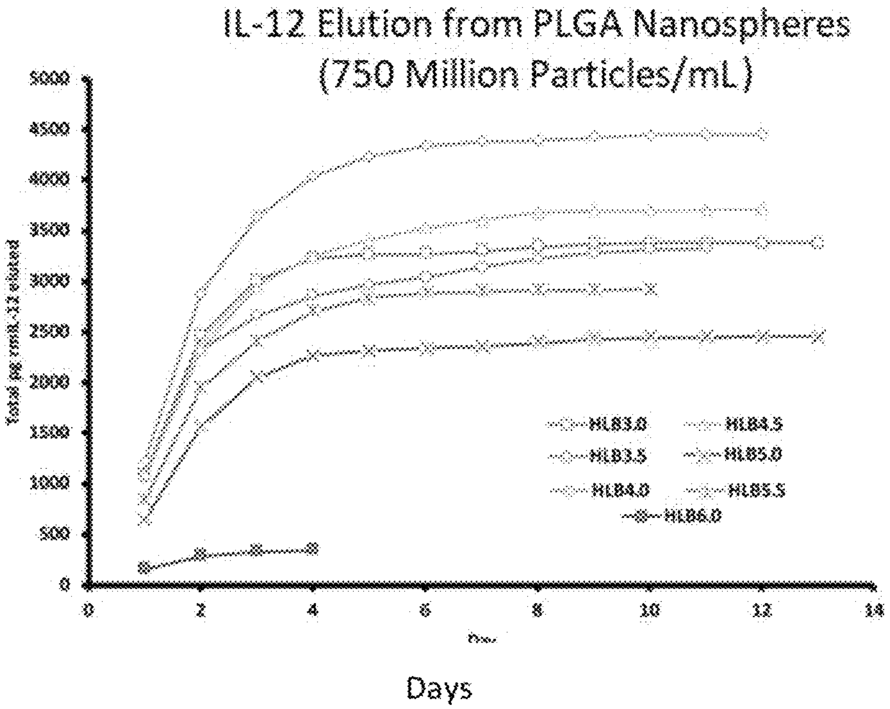
FIG. 10 shows the elution profile of IL-12 from PLGA nanospheres prepared using high-speed stirring, using a nanosphere concentration of 750 million particles/mL, as a function of stirring speed.

As seen in FIG. 10, the elution profile of IL-12 from PLGA nanospheres prepared using high-speed stirring rather than sonication, at a nanosphere concentration of 750 million particles/mL, can be highly dependent on stirring speed. Stirring at 17,500 RPM gives a high encapsulation efficiency, and a total drug release over a 12-day period of about 4500 pg IL-12. Stirring at about 13,000 to about 20,000 RPM gives an acceptable drug release over a 12-day period of about 3500 pg IL-12 or greater. Stirring at greater than about 22,000 RPM gives a low encapsulation efficiency, and a total drug release over a 12-day period of less than 3,000 pg IL-12. The optimum stirring speed for producing IL-12 loaded PLGA nanospheres can be about 17,500 RPM.

Part E. Effect of Nanospheres on Release of a Soluble Cytokine.

Example 10. Release of Free IL-12 vs. Nanosphere-Encapsulated IL-12

Osteosarcoma (OS) induces systemic immune suppression in mice that can be reversed by the checkpoint blocker anti-PD-L1, as shown in FIG. 11. Using anti-PD-L1, their systemic immunophenotype returns to baseline status, relieving immunosuppression from OS. However, baseline status does not provide enough immune stimulation to effectively reduce tumor burden in mice with advanced OS. See FIG. 11, line A. However, patients in a Phase II study of a rituximab/IL-12 combination therapy, where IL-12 was administered as a free peptide, for relapsed and refractory Non-Hodgkin lymphoma (NHL) showed signs of dose-limiting toxicity (DLT). Their immune status, or immunophenotype, was pushed past the level of stimulation and into the realm of a life-threatening state of immune system over-activation known as immune cell exhaustion. See FIG. 11, line C. The goal is to stimulate the immune system above baseline levels, without overstimulation or immune cell exhaustion.

However, in a background of anti-PD-L1 checkpoint blockade providing disinhibition of activated T cells, slow and sustained delivery of low dose IL-12 (which is generally considered safe) from hydrolyzing PLGA nanospheres (IL-12-NS) to the systemic tumor macroenvironment can provide systemic stimulation to effectively reduce tumor burden while still remaining beneath the exhaustion threshold, as shown in FIG. 11, line B. A real-time immunophenotype monitoring platform, like the one described herein, would be of considerable value for this application.

Thus, use of biodegradable PLGA nanospheres as a delivery vehicle for a soluble drug can allow administration of a therapeutically effective low dose. This can be useful where the difference between an effective dosage of a drug and a toxic dose are small.

Part E. Effect of Nanosphere Additives on Release of a Soluble Cytokine.

Example 11

Seven batches of nanospheres containing the drug IL-12 were prepared. The elution profile of these batches was obtained by following the procedure of Example 5, with sonication at 50 Watts power for 10 sec.

Figure 12:
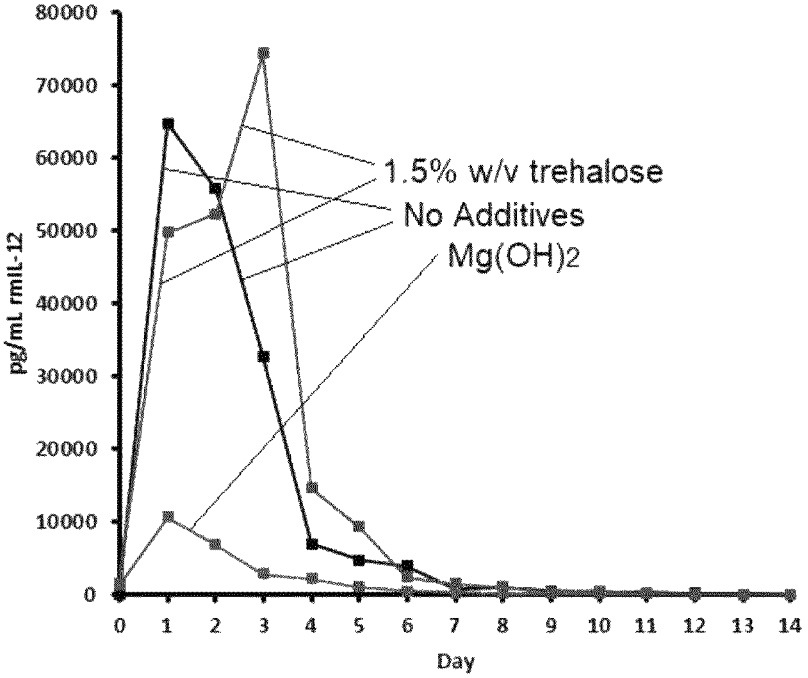
FIG. 12 shows the effect of trehalose and a magnesium compound on IL-12 elution from PLGA nanospheres.

The first batch was made by following the procedure of Example 7, using a protein solution made by suspending 12.5 micrograms of IL-12 in about 20±6 microliters DPBS and a PVA/water phase. No additives not listed in Example 7 were included. Upon elution of the first batch by the method of Example 5, the drug was released with an initial burst phase lasting 1 to 2 days, and a peak IL-12 concentration of –P65,000 pg/mL, reached on the second day, as shown in FIG. 12.

The second batch was made by following the procedure of Example 7, except that a protein solution made by suspending 12.5 micrograms of IL-12 in about 20±6 microliters DPBS containing 1.5% w/trehalose was used. For the second batch, the drug was released with an initial burst phase lasting 3 days, and a peak IL-12 concentration of –P75,000 pg/mL, reached on the third day. As seen in FIG. 12, the presence of trehalose in the protein solution used to make nanospheres significantly increased the overall drug release (measured as area under the curve), compared to drug release from nanospheres made without additional additives.

The third batch was made by following the procedure of Example 7, except that a protein solution made by suspending 12.5 micrograms of IL-12 in about 20±6 microliters DPBS containing 2% w/v $Mg(OH)_2$ was used. Upon elution of the third batch by the method of Example 5, the drug was released with an initial burst phase lasting 1 day, and a peak IL-12 concentration of –P10,000 pg/mL. As seen in FIG. 12, the presence of $Mg(OH)_2$ in the protein solution used to make nanospheres decreased the overall drug release, compared to drug release from nanospheres made without additional additives.

Figure 13:
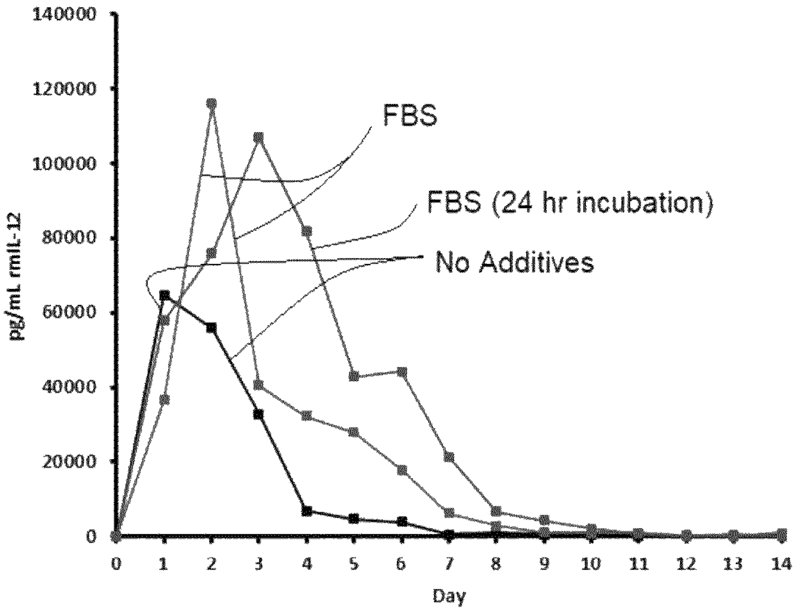
FIG. 13 shows the effect of fetal bovine serum (FBS) on IL-12 elution from PLGA nanospheres.

For the fourth batch, nanospheres were made by following the procedure of Example 7, using a protein solution made by suspending 12.5 micrograms of IL-12 in about 20±6 microliters DPBS containing 10% fetal bovine serum (FBS). Upon elution by the method of Example 5, the drug was released with an initial burst phase lasting 3 days, and a peak IL-12 concentration of –P115,000 pg/mL, reached on the second day. The presence of 10% FBS in the protein solution significantly increased the overall drug release (measured as area under the curve), compared to drug release from nanospheres made without additional additives, as seen in FIG. 13.

For the fifth batch, nanospheres were made by following the procedure of Example 7, using a protein solution made by suspending 12.5 micrograms of IL-12 in about 20±6 microliters DPBS containing 10% fetal bovine serum (FBS), where the protein solution was incubated for 24 hours prior to production of nanospheres. Upon elution by the method of Example 5, the drug was released with an initial burst phase lasting 3 days, and a peak IL-12 concentration of from –P105,000 pg/mL to –P110,000 pg/mL, reached on the third day. As seen in FIG. 13A, the presence of 10% incubated FBS in the protein solution significantly increased the overall drug release from the nanospheres (measured as area under the curve), compared to drug release from either nanospheres made without additional additives, or nanospheres made using FBS in the absence of an incubation step. As seen in the gel elution of FIG. 13B, the incubation of the protein solution for 48 hours prior to the production of nanospheres led to a decrease in total release of IL-12, and lowered the encapsulation efficiency.

For the sixth batch, nanospheres were made by following the procedure of Example 7, using:

a PVA/water phase containing 4% w/v Tween 80; and an oil phase containing 14% w/v Span 60.

Figure 14:
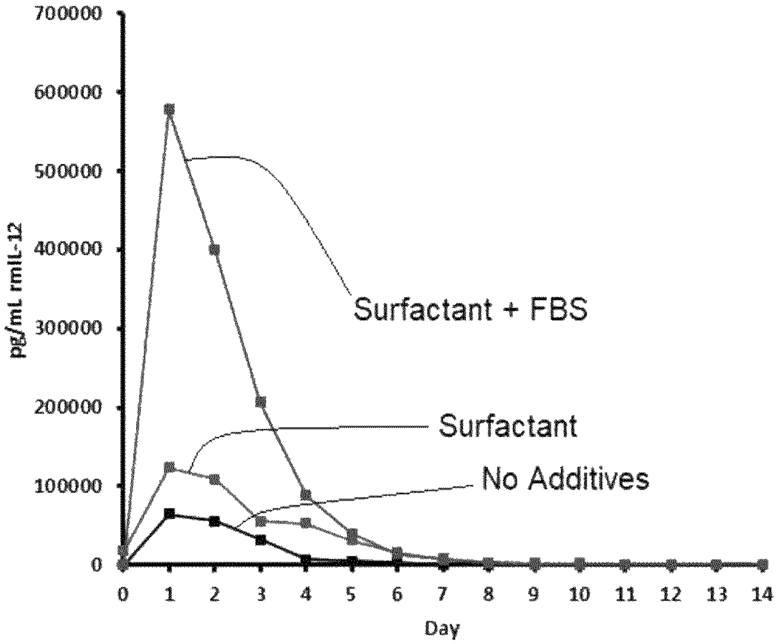
FIG. 14 shows the effect of surfactants, alone or in combination with FBS, on IL-12 elution from PLGA nanospheres.

Upon elution by the method of Example 5, the drug was released with an initial burst phase lasting 1 day, and a peak IL-12 concentration of from −P120,000 pg/mL to −P125,000 pg/mL. As seen in FIG. 14, the presence of Tween 80 and Span 60 surfactants in the protein solution increased the peak drug release from the nanospheres by about a factor of 2, compared to peak drug release from nanospheres made without additional additives. The presence of Tween 80 also substantially increased overall drug release.

For the seventh batch, nanospheres were made by following the procedure of Example 7, using:

a PVA/water phase containing 10% w/v FBS and 4% w/v Tween 80; and an oil phase containing 14% w/v Span 60.

Upon elution by the method of Example 5, the drug was released with an initial burst phase lasting 1 day, and a peak IL-12 concentration of about −580,000 pg/mL. As seen in FIG. 14, the presence of both FBS and surfactants in the protein solution increased the peak drug release from the nanospheres by about a factor of about 9, compared to a peak drug release of −65,000 pg/mL from nanospheres made without additional additives. The presence of both FBS and Tween 80 also:

increased the peak drug release from the nanospheres by about a factor of about 4.5, compared to a peak drug release of −115,000 pg/mL from nanospheres made with FBS alone; and increased the peak drug release from the nanospheres by about a factor of about 4.5, compared to a peak drug release of −120,000 pg/mL from nanospheres made with Tween 80 alone.

TABLE 6

Effect of Nanosphere Additives on Drug Release and Encapsulation Efficiency.

| | Drug Release | | | | |
|---|---|---|---|---|---|
| Additives | Total (pg) | Peak (pg/mL) | Per 100,000 Particles (Pg) | EE (%) | Zeta Potential (mV) |
| None | 289135.30 | 65.000 | .5782 | 8.8 | −36.35 |
| Trehalose | 207386.3905 | 75.000 | 0.414 | 5.79 | −38.95 |
| $Mg(OH)_2$ | 26065.70647 | 10.000 | 0.0521 | 2.19 | −22.4 |
| FBS | 285394.6775 | −115,000 | 0.571 | 6.67 | −36.6 |
| FBS (incubated for 24 h) | 654806.6577 | −110,000 | 1.31 | 35.71 | −39.7 |
| Surfactant* | 419307.8952 | −120.000 | 0.839 | 17.39 | −32.5 |
| Surfactant* + FBS | 1341061.532 | −580,000 | 2.68 | 87.54 | −35.6 |

*Tween 80 + Span 60

Peak drug release, total drug release, drug release/100,000 particles, encapsulation efficiency (EE), and Zeta potential for these modified nanosphere batches are recorded in Table 6. As shown in this table, the peak drug release and the overall drug release upon elution of the drug IL-12 from nanospheres can be increased by making the nanospheres in the presence of an additive selected from the group consisting of trehalose, FBS, FBS with 24 hours incubation, a surfactant, or a mixture thereof. Also, FBS with 24 hours incubation, a surfactant, or a mixture of FBS and a surfactant lead to dramatic increases in encapsulation efficiency. The peak drug release and the overall drug release upon elution can be synergistically increased by making the nanospheres in the presence of both FBS and a surfactant.

Figure 15A:
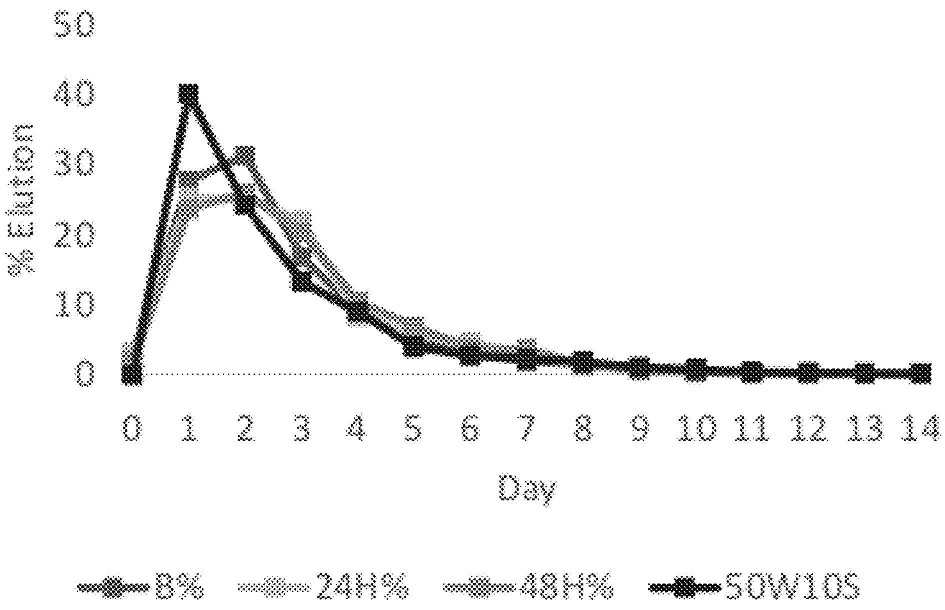
FIGS. 15A and 15B show the percent elution of the protein over time where the nanospheres were prepared under varying conditions and the elution as a percent of total elution, respectively.
Figure 15B:
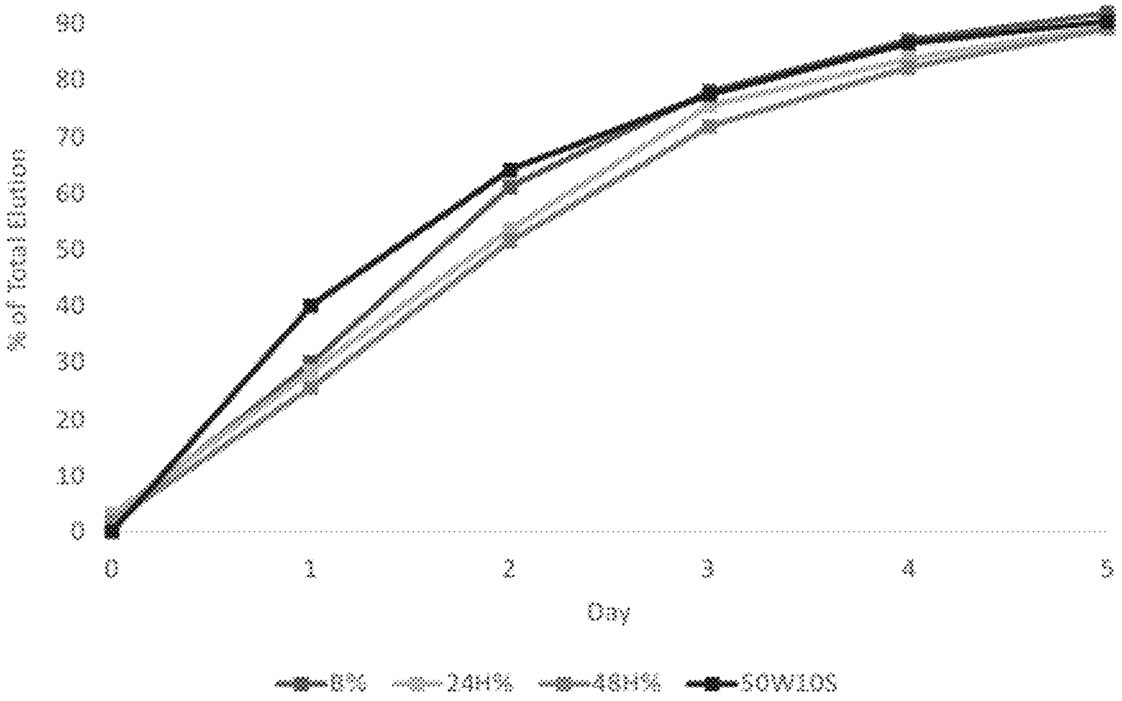

As seen in FIGS. 15A and 15B, batches of nanospheres wherein the solutions were sonicated at 50 W for 10 seconds (50W10S), FBS with no incubation ("baseline") (B), FBS with 24 hour incubation (24 H), and FBS with 48 incubation (48 H) were compared as percent elution (FIG. 15A) and percent of total elution (FIG. 15B). Percent of total allows for accurate comparison of the elution profile versus modified batches. The values for these figures are seen in Table 7. A comparison of the 50W10S elution to the baseline and incubated batches is shown in Table 8.

TABLE 7

Gel elution totals from 10 mg over 14 days and encapsulation efficiencies.

| | TOTAL (pg/mL) | TOTAL (ng/mL) | ng/mL/ batch | ENCAP-SULATION % |
|---|---|---|---|---|
| Baseline FBS.1 | 302893.6686 | 302.8936686 | 2398.917855 | 9.59567142 |
| Baseline FBS.2 | 430181.3177 | 430.1813177 | 2529.466148 | 10.11786459 |
| Baseline FBS AVG | 366537.4931 | 366.5374931 | 2464.192001 | 9.856768006 |
| Incubation: 24.1 h | 717214.2512 | 717.2142512 | 1738.527345 | 6.954109379 |
| Incubation: 24.2 h | 964011.074 | 964.011074 | 2336.762843 | 9.347051374 |
| Incubation: 24 h AVG | 840612.6626 | 840.6126626 | 2037.645094 | 8.150580376 |
| Incubation: 48.1 h | 475557.718 | 475.557718 | 1339.170534 | 5.356682136 |
| Incubation: 48.2 h | 660407.1071 | 660.4071071 | 1859.706414 | 7.438825655 |
| Incubation: 48 h AVG | 567982.4126 | 567.9824126 | 1599.438474 | 6.397753896 |
| MSA/SURF.1 | 1630803.835 | 1630.803835 | 7032.026137 | 28.12810455 |
| MSA/SURF.2 | 1217626.815 | 1217.626815 | 4928.953348 | 19.71581339 |
| MSA/SURF AVG | 1424215.325 | 1424.215325 | 5980.489742 | 23.92195897 |
| FBS/SURF.1 | 1149762.568 | 1149.762568 | 10393.85362 | 41.57541446 |
| FBS/SURF.2 | 1370583.004 | 1370.583004 | 10175.20823 | 40.7008329 |
| FBS/SURF AVG | 1260172.786 | 1260.172786 | 10284.53092 | 41.13812368 |

TABLE 8

Comparison of elution values.

| T TESTS v 50W10S DAY 1-5 | |
|---|---|
| Baseline | 0.37672959 |
| Inc 24 H | 0.06955482 |
| Inc 48 H | 0.03852793 |
| MSA/SURF | 0.03007545 |
| FBS/SURF | 0.02631816 |

TABLE 8-continued

| Comparison of elution values. | |
|---|---|
| T TESTS B v 24/48 DAY 1-5 | |
| Inc 24 H | 0.03282131 |
| Inc 48 H | 0.00907923 |
| T TESTS 24 v 48 DAY 1-5 | |
| Inc 24 H v Inc 48 H | 0.02050595 |

Part F. Effect of IL-12-Loaded Poly(Lactic-Co-Glycolic) Acid (PLGA) Nanospheres on Metastasis and Cure Rate in an Immunocompetent K7M2 Orthotopic Murine Model of Osteosarcoma Mice Male and female BALB/c mice aged 4-5 weeks (Stock Number: 000651) were obtained from The Jackson Laboratory and housed individually in ventilated Allentown cages within specific pathogen-free facilities on corncob bedding with 12 hour light/dark cycles, automatic lixit water, and ad libitum food access. All experiments were approved by the Institutional Animal Care and Use Committee (IACUC).

In Vivo Imaging System (IVIS) Imaging of OS Tumor-Bearing Mice

Animals were IVIS-imaged from the first sign of palpable primary tumor and at weekly intervals thereafter using the IVIS Spectrum CT imaging system (PerkinElmer Life Sciences, Waltham, MA) with Living Image version 4.5 Software to monitor disease burden. At each session, mice received 150 mg/kg i.p. D-luciferin (Caliper Life Sciences, Hopkinton, MA); to visualize metastatic disease in the lung, mice received an additional 15 mg/kg of intranasal D-luciferin (approximately 30 μL). Images were captured using auto-exposure within the predetermined interval of maximum bioluminescence.

Flow Cytometry (FC)

Red blood cells were lysed with Red Blood Cell (RBC) Lysis Solution (Miltenyi Biotec, Auburn, CA). Single cell suspensions were split and incubated with optimized lymphoid (L) and myeloid (M) antibody panels according to the manufacturer's instructions; a minimum of 1×104 events were analyzed for each sample.

Histology

Histology was performed on the lungs of all nIL-12-treated mice that did not have IVIS-positive pulmonary metastases at euthanasia; the metastatic rate of the untreated control group was assessed via a combination of histology and IVIS positivity. Lungs of nIL-12-treated mice were immediately harvested en bloc following euthanasia, placed in neutral buffered formalin, and mounted on a microtome; 50 μm sections were obtained every 250 μm and stained with hematoxylin and eosin, and specimens were analyzed for the presence or absence of metastases by a board-certified pathologist.

Statistical Analysis

To determine significance between categorical clinical data (metastatic and disease-free rates), two-sided chi-squared tests were used. To compare the NK percent populations in peripheral blood between healthy and diseased nIL-12-treated mice, average values for both groups were determined at each time point and the standard deviations (SD) calculated; statistical significance was determined via unpaired two-tailed t tests.

Experimental Design

Thirty male BALB/c mice were cheek bled (red arrows) for 100 μL whole blood before being inoculated intratibially with $1\times10^6$ luc-K7M2 OS tumor cells. The first 12 mice to establish primary tumors were cheek bled again and subsequently randomized into three n=4 nIL-12 dosing groups (low dose; 0.1 mg, medium dose; 1 mg, or high dose; 10 mg). The first dose of nIL-12 (blue arrows) was given via intraperitoneal (i.p.) injection following IVIS-confirmation of primary tumors. Mice were imaged via IVIS and dosed at weekly intervals thereafter, and successive cheek bleeds were performed at weeks 5, 6, 8, 10, and 12. Immediately following the week 12 cheek bleed, mice were euthanized. At week 5, the tumor-bearing limbs were amputated.

In Vivo Induction of Free IL-12 Toxicity in Healthy Mice

Two groups of four BALB/c mice (two female and two male per group) were cheek bled by piercing the facial venous plexus with a sterile 4 mm Goldenrod Animal Lancet (Braintree Scientific. Braintree. MA) to gather 100 μL whole blood for baseline immunophenotyping. Immediately following cheek bleeds, each group was given a retro-orbital (r.o.) injection of either a low (100 ng) or high (100 ug) dose of free recombinant mouse (rm) IL-12 (eBiolegend. San Diego, CA) with 0.1% mouse serum albumin (MSA. Sigma. St. Louis, MO) in 150 μL DPBS. At 24 and 48 hours following r.o, injections, mice underwent additional cheek bleeds for immunophenotyping.

nIL-12 Synthesis nIL-12 nanospheres were prepared using the double emulsion solvent evaporation technique (33). Briefly, 150 μL of 83.3 mg/mL recombinant mouse IL-12 (rmIL-12, (eBiolegend. San Diego, CA) with 10% mouse serum albumin (MSA. Sigma. St. Louis, MO) in DPBS was added to 250 mg PLGA resomer RG 503H (Sigma) dissolved in 1.51 mL dicholoromethane (Sigma) with 14% w/w Span 60 (Sigma); the resulting emulsion was sonicated at 50W for 10 seconds on ice before being added to 5 mL of 1% w/v polyvinyl alcohol (PVA. Sigma) with 4% w/v Tween 80 (Sigma) and sonicated again on ice at the same parameters. The resulting mixture was stirred for three hours at room temperature and washed four times; particles were stored at −80° C., until usage.

K7M2 Syngeneic Orthotopic BALB/c Mouse Model of Metastatic OS

K7M2 murine OS tumor cells (ATCC CRL-2836, ATCC) were kindly donated by Dr. Kurt Weiss. MD (University of Pittsburgh Medical Center. Pittsburgh, PA) in April 2014 and transfected non-virally with the Promega luc2 reporter vector (luc-K7M2) as previously described (34). Luc-K7M2 cells were Mycoplasma free and their identity confirmed in 2018 via IDEXX BioResearch Case #6926-2018 (ID 3). For the orthotopic inoculation, luc-K7M2 cells (1×106) suspended in DMEM media were injected intratibially into 30 mice as previously described (34). Four weeks later, 12 mice with the smallest and most similarly-sized IVIS-confirmed primary tumors were randomized into three log-scale dose treatment groups 1) low dose (0.1 mg nIL-12), 2) medium dose (1 mg nIL-12), and 3) high dose (10 mg nIL-12). One week following IVIS-confirmation of primary tumors, mice underwent amputation of their tumor-bearing limbs as previously described (34). At 12 weeks post-inoculation, mice were euthanized. A schematic of the full experimental design can be seen in FIG. 16.

Time Point Cheek Bleeds in OS Tumor-Bearing Mice

Figure 16:
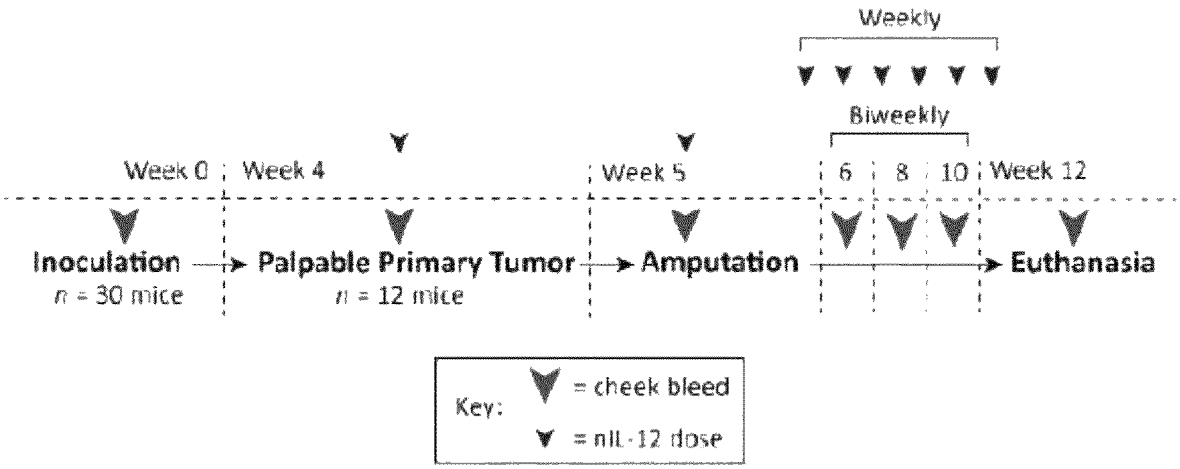
FIG. 16 shows a schematic depicting the experimental design.

Prior to inoculation with tumor cells (week 0), all 30 male BALB/c mice were cheek bled to collect 100 μL whole blood for baseline immunophenotyping. Cheek bleeds were repeated at first sign of palpable primary tumor (week 4), prior to amputation of the affected limb (week five), and again at weeks 6 (T1), 8 (T2), 10 (T3), and 12 (euthanasia/EUTH), as shown in FIG. 16.

nIL-12 Treatment of OS Tumor-Bearing Mice

Twelve tumor-bearing mice were randomized into three n=4 dose groups; 0.1 (low), 1 (medium), or 10 mg (high) of nIL-12 were suspended in 0.1% MSA in sterile DPBS. Mice received their first dose of nIL-12 following IVIS confirmation of palpable primary tumors, and then at weekly time points thereafter for a total of eight doses, as shown in FIG. 16. Each nIL-12 dose was administered intraperitoneal (i.p.) in a total volume of 500 μL.

Figure 17:
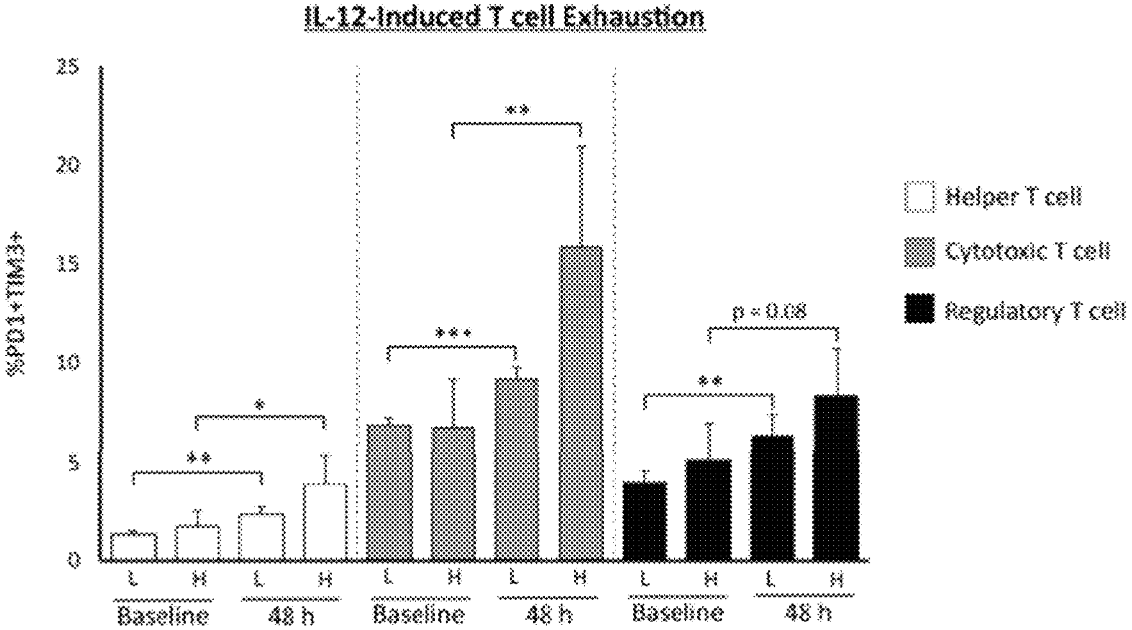
FIG. 17 shows recombinant mouse IL-12 (rmIL-12)-induced T cell exhaustion of helper, cytotoxic, and regulatory T lymphocyte subsets in peripheral blood.

Experiment 12. rmIL-12-Induced T Cell Exhaustion of Helper, Cytotoxic, and Regulatory T Lymphocyte Subsets in Peripheral Blood Twelve BALB/c mice were cheek bled for 100 μL whole blood (baseline) before being dosed with either 100 ng (L: low dose) or 100 μg (H; high dose) of recombinant mouse (rm) IL-12 via retro-orbital (r.o.) injection. Mice were cheek bled again at 24 and 48 hours (48 h), and blood samples were immunophenotyped via flow cytometry. CD8-CD4 helper T cells (left, white), $CD4^-$ $CD8^+$ cytotoxic T cells (middle, gray), and $CD8^-CD4^+FOXP3^+CD25^{+/-}$ regulatory T cells (right, black) were assessed for the extent of $PD1^+TIM\text{-}3^+$ positivity, which can be indicative of exhaustion. Shown in FIG. 17 are T cell data from baseline and 48 h time points. Individual bars (top half) represent group averages+SD. The table (bottom half) shows the group averages±SD for each treatment group and T cell subset. Baseline blood samples (n=4; 2 male and 2 female per group) were compared to 48 h samples using unpaired two-tailed/tests. *p<0.05, p<0.01, *p<0.001.

Figure 18:
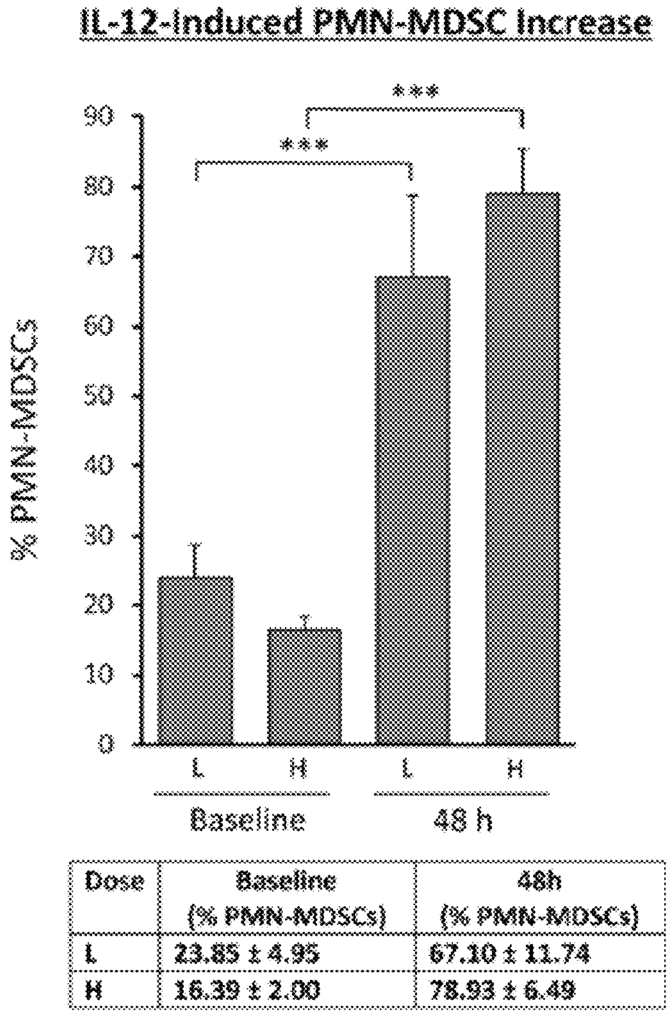
FIG. 18 shows rmIL-12-induced polymorphonuclear-myeloid-derived suppressor cell (PMN-MDSC) myelocytosis in peripheral blood.

Experiment 13. rmIL-12-Induced Polymorphonuclear-Myeloid-Derived Suppressor Cell (PMN-MDSC) Myelocytosis in Peripheral Blood Twelve BALB/c mice were cheek bled for 100 μL whole blood (baseline) before being dosed with either 100 ng (L: low dose) or 100 μg (H: high dose) of recombinant mouse (rm) IL-12 via retro-orbital (r.o.) injection. Mice were cheek bled again at 24 and 48 hours (48 h), and blood samples were immunophenotyped via flow cytometry. Shown in FIG. 18 are PMN-MDSC data from baseline and 48 h time points. Individual bars (top half) represent group averages+SD. The table (bottom half) shows the group averages±SD for each treatment group. Baseline blood samples (n=4; 2 male and 2 female per group) were compared to 48 h samples using unpaired two-tailed/tests. *p<0.05, p<0.01, *p<0.001.

Experiment 14. IL-12-Induced Decrease of Circulating Natural Killer (NK) Cells

Figure 19:
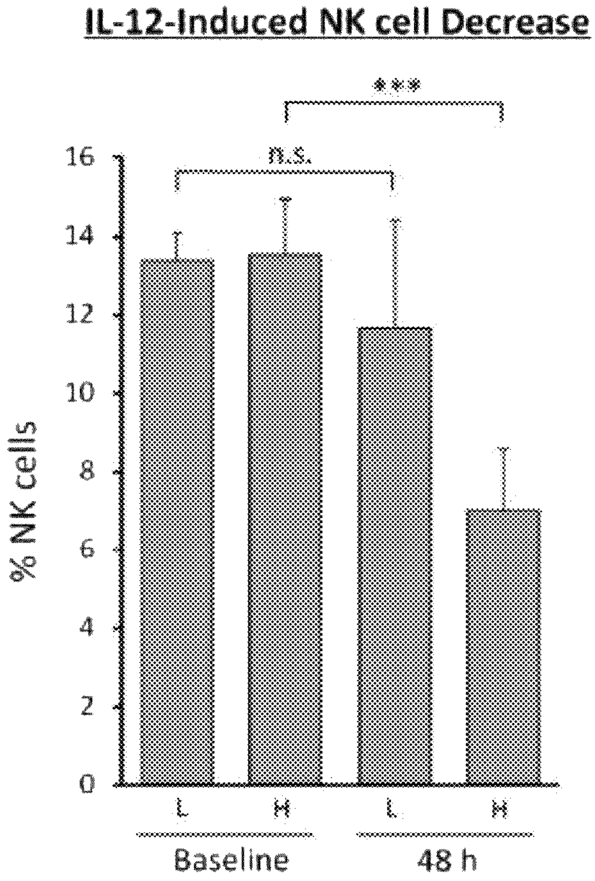
FIG. 19 shows IL-12-induced decrease of circulating Natural Killer (NK) cells.

Twelve BALB/c mice were cheek bled for 100 μL whole blood (baseline) before being dosed with either 100 ng (L: low dose) or 100 μg (H: high dose) of recombinant mouse (rm) IL-12 via retro-orbital (r.o.) injection. Mice were cheek bled again at 24 and 48 hours (48 h), and blood samples were immunophenotyped via flow cytometry. FIG. 19 shows individual bars (top half) represent group averages+S.D. The table (bottom half) shows the group averages±SD for each treatment group. Baseline blood samples (n=4; 2 male and 2 female per group) were compared to 48 h samples using unpaired two-tailed/tests. *p<0.05, p<0.01, *p<0.001.

Figure 20A:
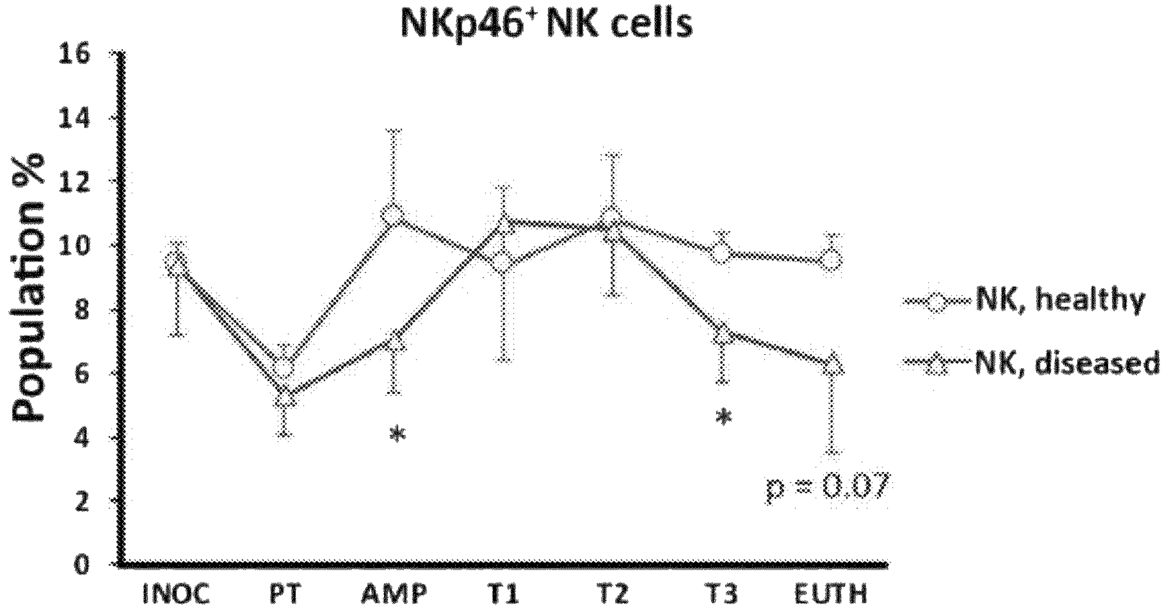
FIGS. 20A and 20B show the average percentage of NKp46+ Natural Killer (NK) cells in the peripheral blood of healthy versus diseased compared across seven time points for 12 weeks and mice stratified upon their NK cell percentages in peripheral blood at amputation, respectively.
Figure 20B:
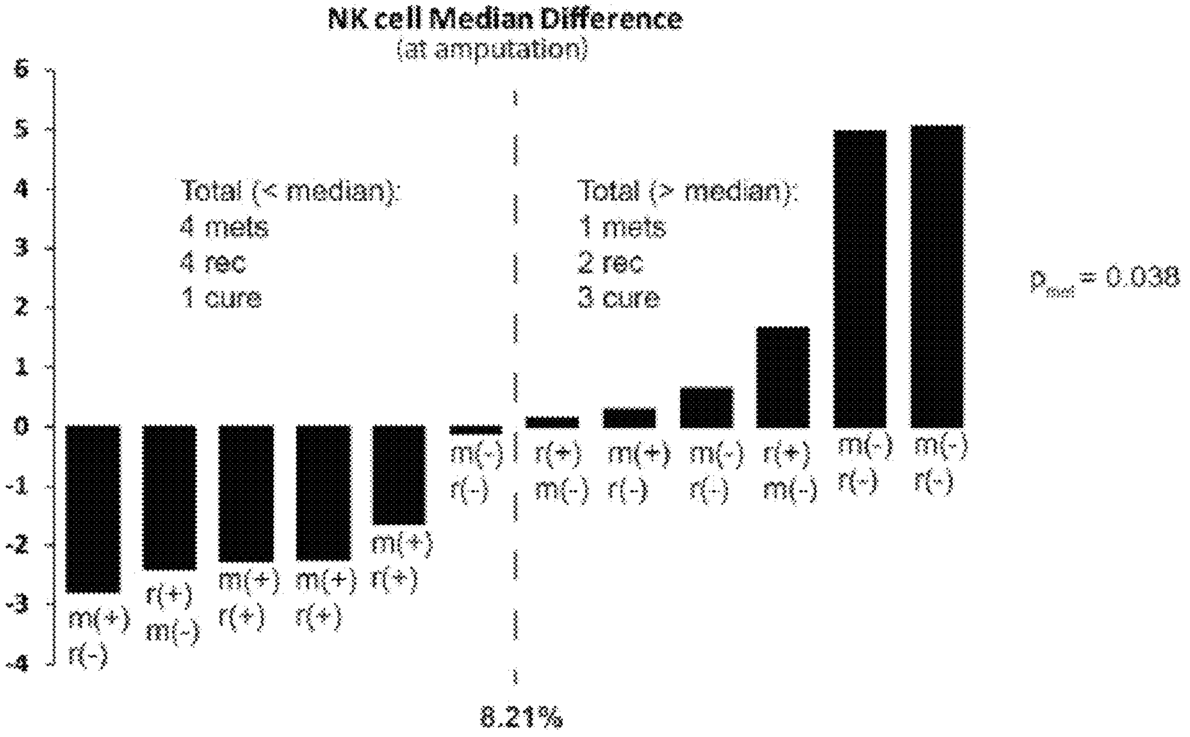

Experiment 15. Blood NK Cell Percentages Above 8.21% at Amputation Separate Non-Metastatic from Metastatic Mice at 12 Weeks nIL-12-treated OS tumor-bearing mice were separated into two groups based upon disease status at 12 weeks including n=8 diseased (metastasis and/or local recurrence positive) and n=4 healthy (both metastasis and local recurrence negative) mice. FIG. 20 shows; (A) average (±SD) percentage of $NKp46^+$ Natural Killer (NK) cells in the peripheral blood of healthy (tumor burden negative at 12 weeks, green circles) versus diseased (tumor burden positive at 12 weeks, red triangles) compared across seven time points for 12 weeks (*p<0.05; , p<0.01; *, p<0.001 using unpaired two-tailed/tests) and (B) mice were stratified based upon their NK cell percentages in peripheral blood at amputation. Each bar represents the extent to which that individual mouse's NK cell percentage deviated from the median value (8.21%). The metastatic rate of mice above the median was compared to that of those below using a one-sided chi-squared test; $p_{met}$=p value for the metastatic rate between groups with NK cell percentages above and below the median at amputation.

What is claimed is:

1. A poly(D,L-lactic acid-co-glycolic acid)(PLGA) nanosphere comprising:

i) PLGA; ii) a water-soluble therapeutic protein; iii) an oil-soluble surfactant; iv) a water-soluble surfactant; v) polyvinyl alcohol (PVA); and vi) a species-specific whole serum, a species-specific engineered serum albumin, or a species-specific native serum albumin.

2. The nanosphere of claim 1, wherein the protein comprises a cytokine.

3. The nanosphere of claim 2, wherein the cytokine comprises an interleukin, a lymphokine, a monokine, an interferon, a colony stimulating factor, a chemokine, or a non-immunological cytokine.

4. The nanosphere of claim 3, wherein the cytokine comprises an interleukin.

5. The nanosphere of claim 4, wherein the interleukin comprises IL-2, IL-3, IL-4, IL-5, IL-6, IL-7, IL-9, IL-10, IL-11, IL-12, the alpha chain of IL-12, IL-13, IL-15, IL-19, IL-20, IL-21, IL-22, IL-23, IL-24, IL-26, or IL-27.

6. The nanosphere of claim 5, wherein the interleukin comprises IL-12.

7. The nanosphere of claim 5, wherein the interleukin comprises IL-2.

8. The nanosphere of claim 1, wherein the oil-soluble surfactant comprises a sorbitan fatty acid ester.

9. The nanosphere of claim 8, wherein the sorbitan fatty acid ester comprises sorbitan monostearate.

10. The nanosphere of claim 1, wherein the water-soluble surfactant comprises a polyoxyethylene sorbitan fatty acid ester.

11. The nanosphere of claim 10, wherein the polyoxyethylene sorbitan fatty acid ester comprises polyoxyethylene sorbitan monooleate.

12. The nanosphere of claim 1, wherein the PLGA comprises from 50% to 75% lactide.

13. The nanosphere of claim 1, wherein the PLGA comprises 50% lactide.

14. The nanosphere of claim 1, wherein the nanosphere comprises the species-specific whole serum.

15. The nanosphere of claim 1, wherein the nanosphere comprises the species-specific engineered serum albumin.

16. The nanosphere of claim 1, wherein the nanosphere comprises the species-specific native serum albumin.

17. The nanosphere of claim 14, wherein the species-specific whole serum comprises a mammalian whole serum.

18. The nanosphere of claim 15, wherein the species-specific engineered serum albumin comprises a mammalian engineered serum albumin.

19. The nanosphere of claim 16, wherein the species-specific native serum albumin comprises a mammalian native serum albumin.

20. The nanosphere of claim 19, wherein the mammalian native serum albumin comprises a human native serum albumin.

21. A dosage form, comprising the nanosphere of claim 1 and a pharmaceutically acceptable excipient.

* * * * *